(12) United States Patent
Pate

(10) Patent No.: US 11,219,745 B2
(45) Date of Patent: Jan. 11, 2022

(54) FISTULA FORMATION DEVICES AND METHODS THEREFOR

(71) Applicant: TVA Medical, Inc., Franklin Lakes, NJ (US)

(72) Inventor: Thomas Diffley Pate, Austin, TX (US)

(73) Assignee: TVA MEDICAL, INC., Franklin Lakes, NJ (US)

( * ) Notice: Subject to any disclaimer, the term of this patent is extended or adjusted under 35 U.S.C. 154(b) by 71 days.

(21) Appl. No.: 16/667,283

(22) Filed: Oct. 29, 2019

(65) Prior Publication Data

US 2020/0061338 A1 Feb. 27, 2020

Related U.S. Application Data

(62) Division of application No. 14/657,997, filed on Mar. 13, 2015, now Pat. No. 10,695,534.

(60) Provisional application No. 61/953,723, filed on Mar. 14, 2014.

(51) Int. Cl.
*A61M 25/01* (2006.01)
*A61B 18/14* (2006.01)
*A61B 17/11* (2006.01)
*A61M 1/36* (2006.01)
(Continued)

(52) U.S. Cl.
CPC ......... *A61M 25/0127* (2013.01); *A61B 17/11* (2013.01); *A61B 18/1492* (2013.01); *A61B 2017/00778* (2013.01); *A61B 2017/00876* (2013.01); *A61B 2018/00345* (2013.01);
(Continued)

(58) Field of Classification Search
CPC . A61M 25/0127; A61M 1/3655; A61B 17/11; A61B 18/1492; A61B 2017/00778
See application file for complete search history.

(56) References Cited

U.S. PATENT DOCUMENTS

| 3,649,850 A | 3/1972 | Davis |
| 3,827,436 A | 8/1974 | Stumpf et al. |
| 4,416,664 A | 11/1983 | Womack |

(Continued)

FOREIGN PATENT DOCUMENTS

| CA | 2883209 A1 | 4/2014 |
| CN | 1730123 A | 2/2006 |

(Continued)

OTHER PUBLICATIONS

Maybury et al., "The Effect of Roll Angle on the Performance of Halbach Arrays," University of California-San Diego, Center for Magnetic Recording Research (2008), 19 pgs.

(Continued)

*Primary Examiner* — Eric D. Bertram
(74) *Attorney, Agent, or Firm* — Dinsmore & Shohl LLP

(57) ABSTRACT

Described here are devices, systems, and methods for forming a fistula between two blood vessels. Generally, the systems may comprise a first catheter and a second catheter, which may comprise one or more fistula-forming elements. The first and second catheters may comprise one or more magnets, which may be used to assist in bringing the first and catheters in closer proximity to facilitate fistula formation. In some variations, the magnet may have a plurality of magnetic domains each characterized by a magnetic flux vector, with the magnetic flux vectors of the magnet passing through a common magnetic origin.

4 Claims, 27 Drawing Sheets

(51) Int. Cl.
   *A61B 18/00*     (2006.01)
   *A61B 17/00*     (2006.01)
(52) U.S. Cl.
   CPC .............. *A61B 2018/00577* (2013.01); *A61B 2018/00595* (2013.01); *A61M 1/3655* (2013.01)

(56) References Cited

U.S. PATENT DOCUMENTS

| | | |
|---|---|---|
| 4,802,475 A | 2/1989 | Weshahy |
| 5,313,943 A | 5/1994 | Houser et al. |
| 5,697,909 A | 12/1997 | Eggers et al. |
| 5,800,487 A | 9/1998 | Mikus et al. |
| 5,830,222 A | 11/1998 | Makower |
| 5,830,224 A | 11/1998 | Cohn et al. |
| 5,895,404 A | 4/1999 | Ruiz |
| 5,971,979 A | 10/1999 | Joye et al. |
| 6,004,330 A | 12/1999 | Middleman et al. |
| 6,032,677 A | 3/2000 | Blechman et al. |
| 6,039,730 A | 3/2000 | Rabin et al. |
| 6,068,638 A | 5/2000 | Makower |
| 6,099,542 A | 8/2000 | Cohn et al. |
| 6,159,225 A | 12/2000 | Makower |
| 6,190,353 B1 | 2/2001 | Makower et al. |
| 6,197,025 B1 | 3/2001 | Grossi et al. |
| 6,217,575 B1 | 4/2001 | DeVore et al. |
| 6,231,587 B1 | 5/2001 | Makower |
| 6,256,525 B1 | 7/2001 | Yang et al. |
| 6,283,988 B1 | 9/2001 | Laufer et al. |
| 6,287,306 B1 | 9/2001 | Kroll et al. |
| 6,302,875 B1 | 10/2001 | Makower et al. |
| 6,327,505 B1 | 12/2001 | Medhkour et al. |
| 6,347,247 B1 | 2/2002 | Dev et al. |
| 6,355,029 B1 | 3/2002 | Joye et al. |
| 6,357,447 B1 | 3/2002 | Swanson et al. |
| 6,379,353 B1 | 4/2002 | Nichols |
| 6,383,180 B1 | 5/2002 | Lalonde et al. |
| 6,400,976 B1 | 6/2002 | Champeau |
| 6,428,534 B1 | 8/2002 | Joye et al. |
| 6,461,356 B1 | 10/2002 | Patterson |
| 6,464,665 B1 | 10/2002 | Heuser |
| 6,464,723 B1 | 10/2002 | Callol |
| 6,468,268 B1 | 10/2002 | Abboud et al. |
| 6,475,214 B1 | 11/2002 | Moaddeb |
| 6,475,226 B1 | 11/2002 | Belef et al. |
| 6,527,724 B1 | 3/2003 | Fenici |
| 6,527,769 B2 | 3/2003 | Langberg et al. |
| 6,542,766 B2 | 4/2003 | Hall et al. |
| 6,544,230 B1 | 4/2003 | Flaherty et al. |
| 6,569,158 B1 | 5/2003 | Abboud et al. |
| 6,569,162 B2 | 5/2003 | He |
| 6,579,311 B1 | 6/2003 | Makower |
| 6,585,650 B1 | 7/2003 | Solem |
| 6,592,577 B2 | 7/2003 | Abboud et al. |
| 6,635,053 B1 | 10/2003 | Lalonde et al. |
| 6,655,386 B1 | 12/2003 | Makower et al. |
| 6,656,173 B1 | 12/2003 | Palermo |
| 6,663,625 B1 | 12/2003 | Ormsby et al. |
| 6,669,709 B1 | 12/2003 | Cohn et al. |
| 6,673,085 B1 | 1/2004 | Berg |
| 6,676,657 B2 | 1/2004 | Wood |
| 6,682,525 B2 | 1/2004 | Lalonde et al. |
| 6,695,878 B2 | 2/2004 | McGuckin et al. |
| 6,709,444 B1 | 3/2004 | Makower |
| 6,719,756 B1 | 4/2004 | Muntermann |
| 6,726,697 B2 | 4/2004 | Nicholas et al. |
| 6,733,494 B2 | 5/2004 | Abboud et al. |
| 6,736,808 B1 | 5/2004 | Motamedi et al. |
| 6,761,708 B1 | 7/2004 | Chiu et al. |
| 6,761,714 B2 | 7/2004 | Abboud et al. |
| 6,780,181 B2 | 8/2004 | Kroll et al. |
| 6,849,073 B2 | 2/2005 | Hoey et al. |
| 6,855,143 B2 | 2/2005 | Davison et al. |
| 6,887,234 B2 | 5/2005 | Abboud et al. |
| 6,911,026 B1 | 6/2005 | Hall et al. |
| 6,932,814 B2 | 8/2005 | Wood |
| 6,936,024 B1 | 8/2005 | Houser |
| 6,960,209 B2 | 11/2005 | Clague et al. |
| 6,971,983 B1 | 12/2005 | Cancio |
| 6,981,972 B1 | 1/2006 | Farley et al. |
| 7,059,330 B1 | 6/2006 | Makower et al. |
| 7,060,063 B2 | 6/2006 | Marion et al. |
| 7,094,235 B2 | 8/2006 | Francischelli |
| 7,155,293 B2 | 12/2006 | Westlund et al. |
| 7,179,270 B2 | 2/2007 | Makower |
| 7,189,231 B2 | 3/2007 | Clague et al. |
| 7,214,234 B2 | 5/2007 | Rapacki et al. |
| 7,231,260 B2 | 6/2007 | Wallace et al. |
| 7,250,051 B2 | 7/2007 | Francischelli |
| 7,288,075 B2 | 10/2007 | Parihar et al. |
| 7,303,554 B2 | 12/2007 | Lalonde et al. |
| 7,306,598 B2 | 12/2007 | Truckai et al. |
| 7,335,198 B2 | 2/2008 | Eggers et al. |
| 7,341,063 B2 | 3/2008 | Garbibaldi et al. |
| 7,367,341 B2 | 5/2008 | Anderson et al. |
| 7,374,567 B2 | 5/2008 | Heuser |
| 7,387,636 B2 | 6/2008 | Cohn et al. |
| 7,407,506 B2 | 8/2008 | Makower |
| 7,628,768 B2 | 12/2009 | Faul et al. |
| 7,702,387 B2 | 4/2010 | Stevenson et al. |
| 7,727,268 B2 | 6/2010 | Cunniffe et al. |
| 7,744,596 B2 | 6/2010 | Young et al. |
| 7,811,281 B1 | 10/2010 | Rentrop |
| 7,828,814 B2 | 11/2010 | Brenneman et al. |
| 7,846,172 B2 | 12/2010 | Makower |
| 7,849,860 B2 | 12/2010 | Makower et al. |
| 7,857,809 B2 | 12/2010 | Drysen |
| 7,881,797 B2 | 2/2011 | Griffin et al. |
| 7,955,326 B2 | 6/2011 | Paul et al. |
| 7,967,769 B2 | 6/2011 | Faul et al. |
| 7,967,770 B2 | 6/2011 | Li et al. |
| 8,010,208 B2 | 8/2011 | Nimer et al. |
| 8,048,016 B2 | 11/2011 | Faul et al. |
| 8,052,680 B2 | 11/2011 | Hassett et al. |
| 8,062,321 B2 | 11/2011 | Heuser et al. |
| RE43,007 E | 12/2011 | Lalonde et al. |
| 8,075,555 B2 | 12/2011 | Truckai et al. |
| 8,088,171 B2 | 1/2012 | Brenneman |
| 8,100,899 B2 | 1/2012 | Doty et al. |
| 8,118,809 B2 | 2/2012 | Paul et al. |
| 8,135,467 B2 | 3/2012 | Markowitz et al. |
| 8,142,454 B2 | 3/2012 | Harrison et al. |
| 8,192,425 B2 | 6/2012 | Mirza et al. |
| 8,200,466 B2 | 6/2012 | Spilker et al. |
| 8,226,592 B2 | 7/2012 | Brenneman et al. |
| 8,231,618 B2 | 7/2012 | Viswanathan et al. |
| 8,236,014 B2 | 8/2012 | Brenneman et al. |
| 8,262,649 B2 | 9/2012 | Francischelli |
| 8,273,095 B2 | 9/2012 | Brenneman et al. |
| 8,328,797 B2 | 12/2012 | Wilson et al. |
| 8,333,758 B2 | 12/2012 | Joye et al. |
| 8,361,061 B2 | 1/2013 | Esch et al. |
| 8,366,707 B2 | 2/2013 | Kassab et al. |
| 8,382,697 B2 | 2/2013 | Brenneman et al. |
| 8,409,196 B2 | 4/2013 | Durgin et al. |
| 8,413,664 B2 | 4/2013 | Appling |
| 8,414,572 B2 | 4/2013 | Davison et al. |
| 8,419,681 B2 | 4/2013 | Sell |
| 8,439,909 B2 | 5/2013 | Wang et al. |
| 8,454,587 B2 | 6/2013 | Lalonde et al. |
| 8,475,441 B2 | 7/2013 | Babkin et al. |
| 8,486,062 B2 | 7/2013 | Belhe et al. |
| 8,486,064 B2 | 7/2013 | Van Wyk et al. |
| 8,551,032 B2 | 10/2013 | Faul et al. |
| 8,574,185 B2 | 11/2013 | Faul et al. |
| 8,585,700 B2 | 11/2013 | Katou |
| 8,608,754 B2 | 12/2013 | Wensel et al. |
| 8,641,724 B2 | 2/2014 | Brenneman et al. |
| 8,649,879 B2 | 2/2014 | DiGiore et al. |
| 8,676,309 B2 | 3/2014 | Deem et al. |
| 8,685,014 B2 | 4/2014 | Babkin et al. |
| 8,700,179 B2 | 4/2014 | Pianca et al. |
| 8,715,281 B2 | 5/2014 | Barlow et al. |
| 8,758,334 B2 | 6/2014 | Coe et al. |

(56) References Cited

U.S. PATENT DOCUMENTS

| | | |
|---|---|---|
| 8,771,267 B2 | 7/2014 | Kunis et al. |
| 8,784,409 B2 | 7/2014 | Robilotto et al. |
| 8,790,341 B2 | 7/2014 | Pappone et al. |
| 8,876,699 B2 | 11/2014 | Sato et al. |
| 8,876,815 B2 | 11/2014 | Coe et al. |
| 8,882,765 B2 | 11/2014 | Kassab et al. |
| 8,911,435 B2 | 12/2014 | Katoh et al. |
| 8,951,251 B2 | 2/2015 | Willard |
| 9,017,323 B2 | 4/2015 | Miller et al. |
| 9,039,702 B2* | 5/2015 | Miller ............ A61B 17/320725 606/41 |
| 9,072,880 B2 | 7/2015 | Phillips et al. |
| 9,089,316 B2 | 7/2015 | Baust et al. |
| 9,108,018 B2 | 8/2015 | Dickinson et al. |
| 9,155,827 B2 | 10/2015 | Franano |
| 9,204,916 B2 | 12/2015 | Lalonde |
| 9,259,340 B2 | 2/2016 | Heuser et al. |
| 9,283,034 B2 | 3/2016 | Katoh et al. |
| 9,307,992 B2 | 4/2016 | Wilson et al. |
| 9,314,329 B2 | 4/2016 | Dickinson et al. |
| 9,326,792 B2 | 5/2016 | Dickinson et al. |
| 9,364,280 B2 | 6/2016 | Zarins et al. |
| 9,402,560 B2 | 8/2016 | Organ et al. |
| 9,414,885 B2 | 8/2016 | Willard |
| 9,439,728 B2 | 9/2016 | Hull et al. |
| 9,445,868 B2 | 9/2016 | Hull et al. |
| 9,452,015 B2 | 9/2016 | Kellerman et al. |
| 9,486,276 B2* | 11/2016 | Rios ..................... A61M 25/01 |
| 9,623,217 B2 | 4/2017 | Pillai |
| 9,706,998 B2 | 7/2017 | Dickinson et al. |
| 9,782,201 B2 | 10/2017 | Dickinson et al. |
| 9,782,533 B2 | 10/2017 | Brenneman et al. |
| 10,045,817 B2 | 8/2018 | Miller et al. |
| 10,265,206 B2 | 4/2019 | Heuser et al. |
| 10,517,637 B2 | 12/2019 | Dickinson et al. |
| 10,543,308 B2 | 1/2020 | Lenihan et al. |
| 10,575,974 B2 | 3/2020 | De Pablo Pena et al. |
| 10,596,356 B2 | 3/2020 | Lenihan et al. |
| 10,821,217 B2* | 11/2020 | Pate ........................ A61B 34/73 |
| 10,869,717 B2* | 12/2020 | Rios ............... A61B 17/320016 |
| 2001/0029384 A1 | 10/2001 | Nicholas et al. |
| 2002/0072739 A1 | 6/2002 | Lee et al. |
| 2002/0113678 A1 | 8/2002 | Creighton |
| 2002/0151945 A1 | 10/2002 | Gobin et al. |
| 2003/0009163 A1 | 1/2003 | Messing et al. |
| 2003/0220674 A1 | 11/2003 | Anderson et al. |
| 2004/0059211 A1 | 3/2004 | Patel et al. |
| 2004/0059280 A1 | 3/2004 | Makower et al. |
| 2004/0167506 A1 | 8/2004 | Chen |
| 2004/0215220 A1 | 10/2004 | Dolan et al. |
| 2004/0236360 A1 | 11/2004 | Cohn et al. |
| 2005/0033401 A1 | 2/2005 | Cunniffe et al. |
| 2005/0065509 A1 | 3/2005 | Coldwell et al. |
| 2005/0245925 A1 | 11/2005 | Iki et al. |
| 2005/0251120 A1 | 11/2005 | Anderson et al. |
| 2006/0079897 A1 | 4/2006 | Harrison et al. |
| 2006/0111704 A1 | 5/2006 | Brenneman et al. |
| 2007/0173878 A1 | 7/2007 | Heuser |
| 2007/0185567 A1 | 8/2007 | Heuser et al. |
| 2007/0203515 A1 | 8/2007 | Heuser et al. |
| 2007/0203572 A1 | 8/2007 | Heuser et al. |
| 2007/0293856 A1 | 12/2007 | Paul et al. |
| 2008/0021532 A1 | 1/2008 | Kveen et al. |
| 2008/0051626 A1 | 2/2008 | Sato et al. |
| 2008/0065019 A1 | 3/2008 | Heuser et al. |
| 2008/0091192 A1 | 4/2008 | Paul et al. |
| 2008/0119879 A1 | 5/2008 | Brenneman et al. |
| 2008/0140061 A1 | 6/2008 | Toubia et al. |
| 2008/0161901 A1 | 7/2008 | Heuser et al. |
| 2008/0171944 A1 | 7/2008 | Brenneman et al. |
| 2008/0183164 A1 | 7/2008 | Elkins et al. |
| 2008/0188848 A1 | 8/2008 | Deutmeyer et al. |
| 2008/0275442 A1 | 11/2008 | Paul et al. |
| 2008/0312577 A1 | 12/2008 | Drasler et al. |
| 2009/0036872 A1 | 2/2009 | Fitzgerald et al. |
| 2009/0076324 A1 | 3/2009 | Takayama et al. |
| 2009/0093791 A1 | 4/2009 | Heuser |
| 2009/0112119 A1 | 4/2009 | Kim |
| 2009/0118722 A1 | 5/2009 | Ebbers et al. |
| 2009/0124847 A1 | 5/2009 | Doty et al. |
| 2009/0157014 A1 | 6/2009 | Osborne et al. |
| 2009/0198232 A1 | 8/2009 | Young et al. |
| 2009/0248148 A1 | 10/2009 | Shaolian et al. |
| 2009/0275876 A1 | 11/2009 | Brenneman et al. |
| 2009/0281379 A1 | 11/2009 | Binmoeller et al. |
| 2009/0318849 A1 | 12/2009 | Hobbs et al. |
| 2010/0004623 A1 | 1/2010 | Hamilton, Jr. et al. |
| 2010/0010488 A1 | 1/2010 | Kassab et al. |
| 2010/0082058 A1 | 4/2010 | Kassab |
| 2010/0130835 A1 | 5/2010 | Brenneman et al. |
| 2010/0198206 A1 | 8/2010 | Levin |
| 2010/0204691 A1 | 8/2010 | Bencini |
| 2010/0222664 A1 | 9/2010 | Lemon et al. |
| 2010/0256616 A1 | 10/2010 | Katoh et al. |
| 2010/0280316 A1 | 11/2010 | Dietz et al. |
| 2010/0280514 A1 | 11/2010 | Zerfas et al. |
| 2010/0286705 A1 | 11/2010 | Vassiliades, Jr. |
| 2010/0292685 A1 | 11/2010 | Katoh et al. |
| 2010/0298645 A1 | 11/2010 | Deutch |
| 2010/0318180 A1 | 12/2010 | Porter |
| 2011/0015657 A1 | 1/2011 | Brenneman et al. |
| 2011/0112427 A1 | 5/2011 | Phillips et al. |
| 2011/0118735 A1 | 5/2011 | Abou-Marie et al. |
| 2011/0201990 A1 | 8/2011 | Franano |
| 2011/0213309 A1 | 9/2011 | Young et al. |
| 2011/0218476 A1 | 9/2011 | Kraemer et al. |
| 2011/0270149 A1 | 11/2011 | Faul et al. |
| 2011/0288392 A1 | 11/2011 | de la Rama et al. |
| 2011/0288544 A1 | 11/2011 | Verin et al. |
| 2011/0306959 A1 | 12/2011 | Kellerman et al. |
| 2011/0306993 A1 | 12/2011 | Hull et al. |
| 2011/0319976 A1 | 12/2011 | Iyer et al. |
| 2012/0010556 A1 | 1/2012 | Faul et al. |
| 2012/0022518 A1 | 1/2012 | Levinson |
| 2012/0035539 A1 | 2/2012 | Tegg |
| 2012/0046678 A1 | 2/2012 | LeMaitre et al. |
| 2012/0059398 A1 | 3/2012 | Pate et al. |
| 2012/0065652 A1 | 3/2012 | Cully et al. |
| 2012/0078342 A1 | 3/2012 | Vollkron et al. |
| 2012/0089123 A1 | 4/2012 | Organ et al. |
| 2012/0101423 A1 | 4/2012 | Brenneman |
| 2012/0116354 A1 | 5/2012 | Heuser |
| 2012/0157992 A1 | 6/2012 | Smith et al. |
| 2012/0209377 A1 | 8/2012 | Machold et al. |
| 2012/0215088 A1 | 8/2012 | Wang et al. |
| 2012/0239021 A1 | 9/2012 | Doty et al. |
| 2012/0277736 A1 | 11/2012 | Francischelli |
| 2012/0281330 A1 | 11/2012 | Abbott et al. |
| 2012/0289953 A1 | 11/2012 | Berzak et al. |
| 2012/0296262 A1 | 11/2012 | Ogata et al. |
| 2012/0302935 A1* | 11/2012 | Miller ................ A61B 18/1492 604/8 |
| 2013/0041306 A1 | 2/2013 | Faul et al. |
| 2013/0056876 A1 | 3/2013 | Harvey et al. |
| 2013/0110105 A1 | 5/2013 | Vankov |
| 2013/0172881 A1 | 7/2013 | Hill et al. |
| 2013/0190744 A1 | 7/2013 | Avram et al. |
| 2013/0190754 A1 | 7/2013 | Paul et al. |
| 2013/0216351 A1 | 8/2013 | Griffin |
| 2013/0226170 A1 | 8/2013 | Seddon et al. |
| 2013/0261368 A1 | 10/2013 | Schwartz |
| 2013/0282000 A1 | 10/2013 | Parsonage |
| 2014/0031674 A1 | 1/2014 | Newman et al. |
| 2014/0094791 A1 | 4/2014 | Hull et al. |
| 2014/0100557 A1 | 4/2014 | Bohner et al. |
| 2014/0100562 A1 | 4/2014 | Sutermeister et al. |
| 2014/0107642 A1 | 4/2014 | Rios et al. |
| 2014/0166098 A1 | 6/2014 | Kian et al. |
| 2014/0188028 A1 | 7/2014 | Brenneman et al. |
| 2014/0276335 A1 | 9/2014 | Pate |
| 2015/0005759 A1 | 1/2015 | Welches et al. |
| 2015/0011909 A1 | 1/2015 | Holmin et al. |
| 2015/0018810 A1 | 1/2015 | Baust et al. |
| 2015/0057654 A1 | 2/2015 | Leung et al. |

(56) References Cited

U.S. PATENT DOCUMENTS

| | | |
|---|---|---|
| 2015/0057687 A1 | 2/2015 | Gittard et al. |
| 2015/0080886 A1 | 3/2015 | Miller et al. |
| 2015/0094645 A1 | 4/2015 | Omar-Pasha |
| 2015/0112195 A1 | 4/2015 | Berger et al. |
| 2015/0126965 A1 | 5/2015 | Liungman |
| 2015/0134055 A1 | 5/2015 | Spence et al. |
| 2015/0141836 A1 | 5/2015 | Naumann et al. |
| 2015/0164573 A1 | 6/2015 | Delaney |
| 2015/0196356 A1 | 7/2015 | Kauphusman et al. |
| 2015/0196360 A1 | 7/2015 | Grantham et al. |
| 2015/0201962 A1 | 7/2015 | Kellerman et al. |
| 2015/0258308 A1 | 9/2015 | Pate |
| 2015/0297259 A1 | 10/2015 | Matsubara et al. |
| 2015/0313668 A1 | 11/2015 | Miller et al. |
| 2015/0320472 A1 | 11/2015 | Ghaffar et al. |
| 2016/0022345 A1 | 1/2016 | Baust et al. |
| 2016/0058452 A1 | 3/2016 | Brenneman et al. |
| 2016/0058956 A1 | 3/2016 | Cohn et al. |
| 2016/0067449 A1 | 3/2016 | Misener et al. |
| 2016/0082234 A1 | 3/2016 | Schwartz et al. |
| 2016/0128855 A1 | 5/2016 | Heuser et al. |
| 2016/0135881 A1 | 5/2016 | Katoh et al. |
| 2016/0184011 A1 | 6/2016 | Krishnan |
| 2016/0206317 A1 | 7/2016 | Dickinson et al. |
| 2017/0119464 A1 | 5/2017 | Rios et al. |
| 2017/0172679 A1 | 6/2017 | Doty et al. |
| 2017/0202603 A1 | 7/2017 | Cohn et al. |
| 2017/0202616 A1 | 7/2017 | Pate et al. |
| 2018/0000512 A1 | 1/2018 | Dickinson et al. |
| 2018/0083228 A1 | 3/2018 | Yang et al. |
| 2018/0116522 A1 | 5/2018 | Brenneman et al. |
| 2018/0206845 A1 | 7/2018 | Brenneman et al. |
| 2018/0344396 A1 | 12/2018 | Miller et al. |
| 2020/0061338 A1 | 2/2020 | Pate |

FOREIGN PATENT DOCUMENTS

| | | |
|---|---|---|
| CN | 101730557 A | 6/2010 |
| EP | 0923912 A2 | 6/1999 |
| RU | 2168951 C1 | 6/2001 |
| WO | 9956640 A1 | 11/1999 |
| WO | 2006105008 A1 | 10/2006 |
| WO | 2008010039 A2 | 1/2008 |
| WO | 2009005644 A2 | 1/2009 |
| WO | 2011100625 A2 | 8/2011 |
| WO | 2013112584 A1 | 8/2013 |
| WO | 2014052919 A1 | 4/2014 |
| WO | 2015061614 A1 | 4/2015 |
| WO | 2015085119 A1 | 6/2015 |
| WO | 2015108984 A1 | 7/2015 |
| WO | 2016033380 A1 | 3/2016 |
| WO | 2017124059 A1 | 7/2017 |
| WO | 2017124060 A1 | 7/2017 |
| WO | 2018057095 A1 | 3/2018 |

OTHER PUBLICATIONS

Choi, et al., Design of a Halbach Magnet Array Based on Optimization Techniques; IEEE Transactions on Magnetics, vol. 44, No. 10, Oct. 2008, pp. 2361-2366. (Year: 2008).

"Banasik et al. (2011). ""A rare variant route of the ulnar artery does not contraindicate the creation of a fistula in the wrist of a diabetic patient with end-stage renal disease,"" Postepy Hig Med Dosw. 65:654-657."

Bharat et al. (2012) "A novel technique of vascular anastomosis to prevent juxta-anastomotic stenosis following arteriovenous fistula creation," J. Vascular Surgery 55(1):274-280.

Bode et al. (2011 ). "Clinical study protocol for the arch project Computational modeling for improvement of outcome after vascular access creation," J. Vase. Access 12(4):369-376.

Davidson, I. et al. (2008). "Duplex Ultrasound Evaluation for Dialysis Access Selection and Maintenance: A Practical Guide," The Journal of Vascular Access 9(1 ): 1-9.

Gracz, et al. (1977). "Proximal forearm fistula for maintenance hemodialysis," Kidney International 11 :71-75.

Jennings, WC. et al. (2011). "Primary arteriovenous fistula inflow proximalization for patients at high risk for dialysis access-associated ischemic steal syndrome," J Vase. Surgery 54(2):554-558.

Kinnaert, et al. (1971). "Ulnar Arteriovenous Fistula for Maintenance Haemodial Ysis," British J. Surgery 58(9):641-643.

Morale et al. (2011). "Venae comitantes as a potential vascular resource to create native arteriovenous fistulae," J. Vase. Access 12(3):211-214.

Shenoy, S. (2009). "Surgical anatomy of upper arm: what is needed for AVF planning," The Journal of Vascular Access 10:223-232.

Vachharajani, T. (2010). "Atlas of Dialysis Vascular Access," Wake Forest University School of Medicine, 77 total pages.

Whittaker et al. (2011). "Prevention better than cure. Avoiding steal syndrome with proximal radial or ulnar arteriovenous fistulae" J. Vase. Access 12(4):318-320.

Hakim et al., "Ulnar artery-based free forearm flap: Review of Specific anatomic features in 322 cases and related literature," Heand & Neck, Dec. 2013 (published online:2014), Wiley Online Library.

Extended European Search Report for EP Application No. 17739123.2.

Extended European Search Report pertaining to EP Patent Application No. 17853586.0, dated Apr. 29, 2020.

Office Action pertaining to corresponding Japanese Patent Application No. 2018-536423, dated Feb. 12, 2021.

* cited by examiner

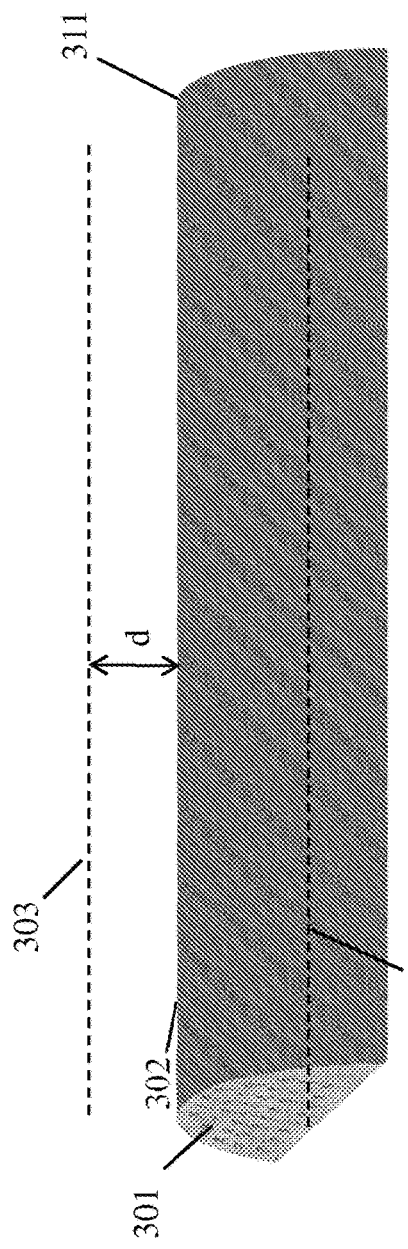
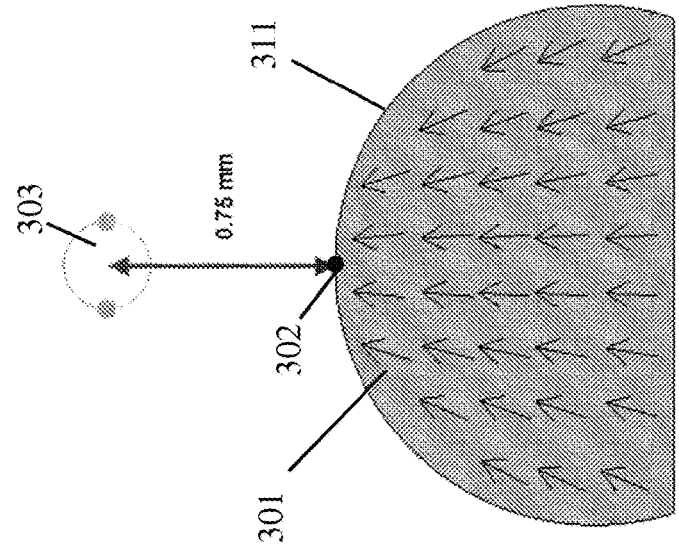

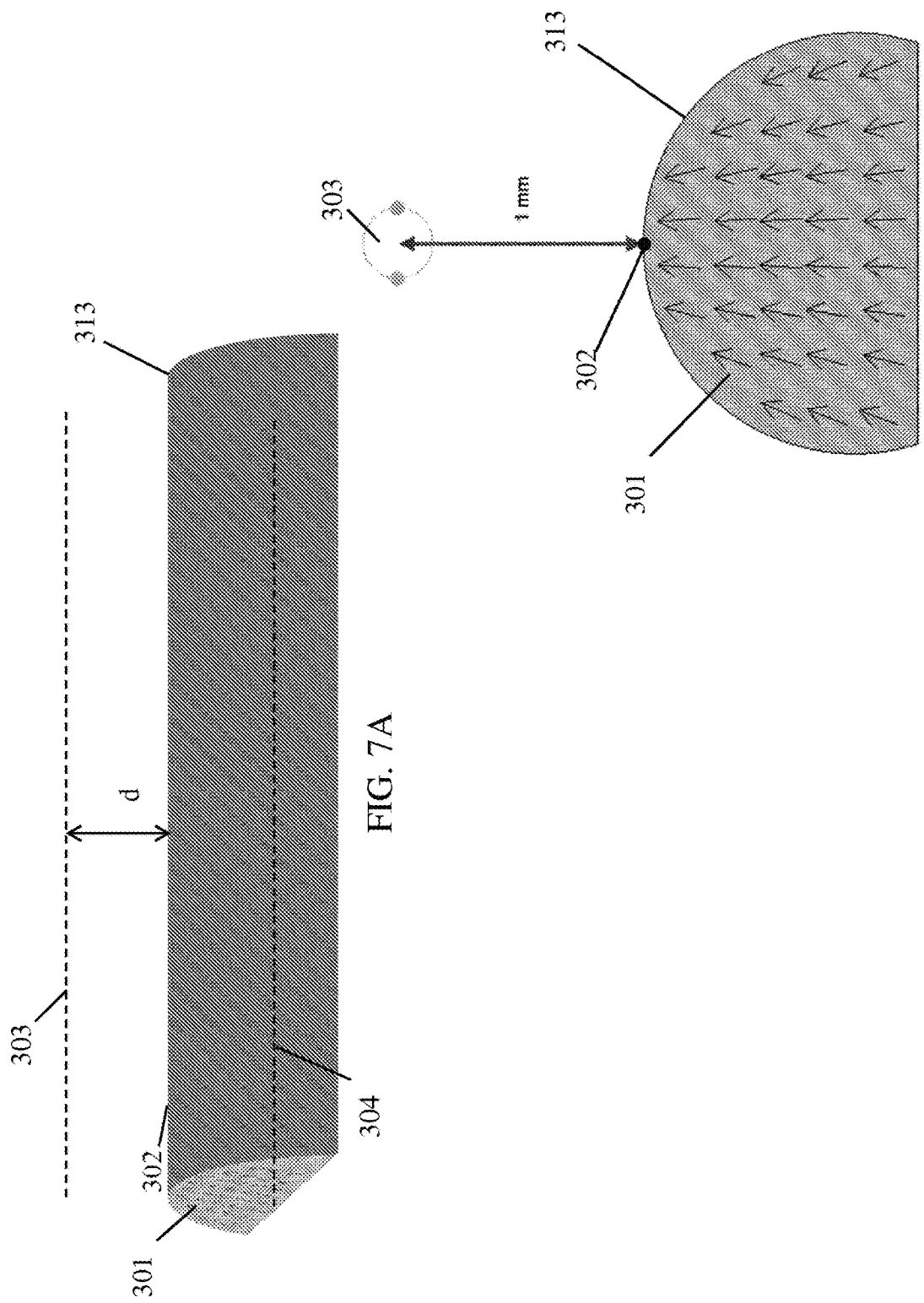

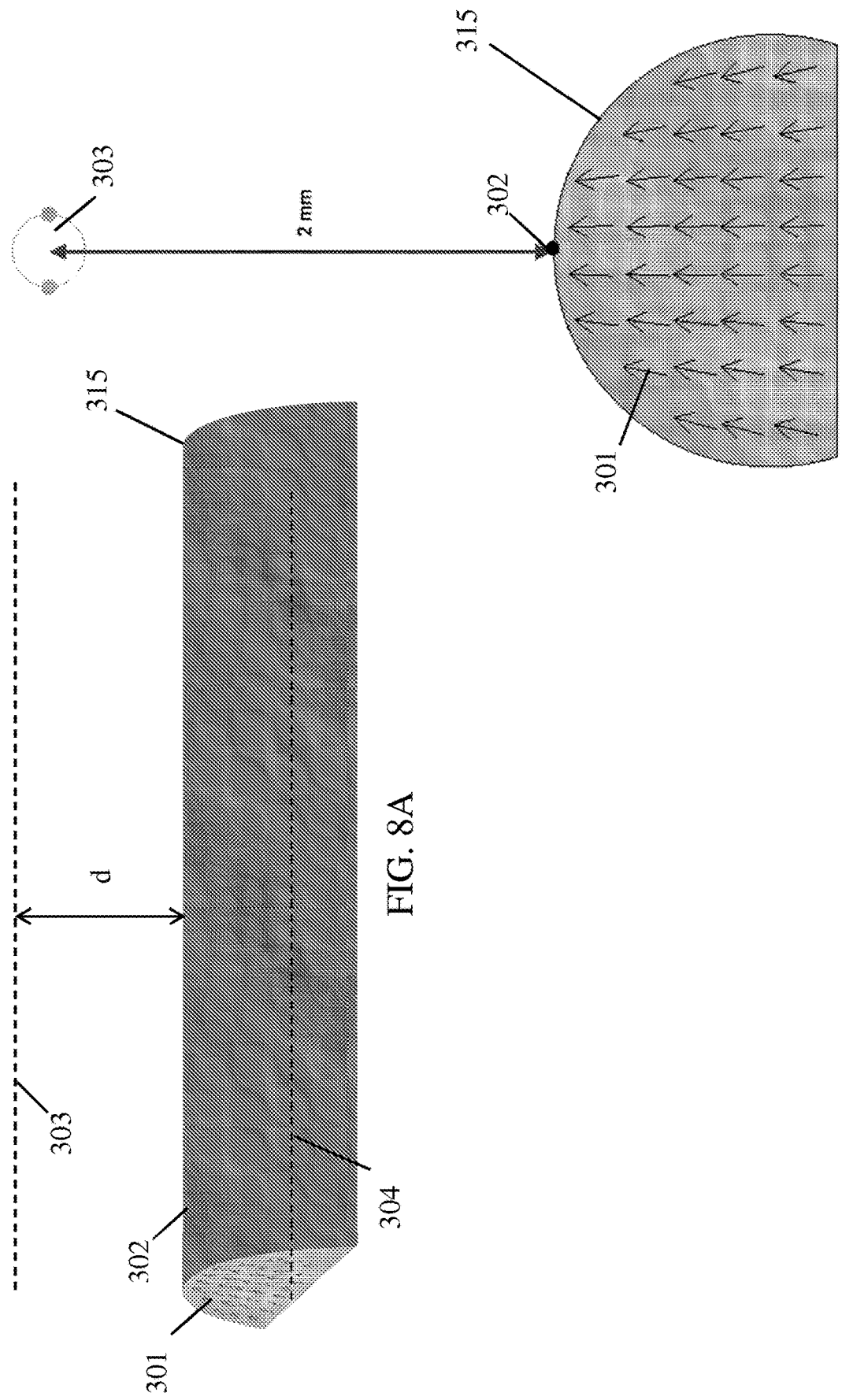

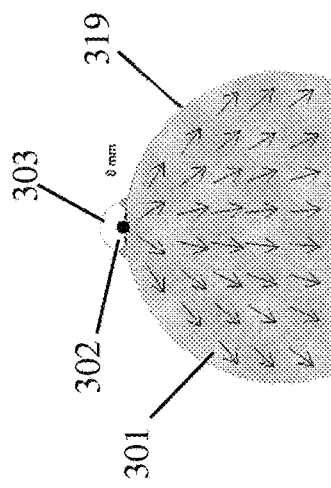
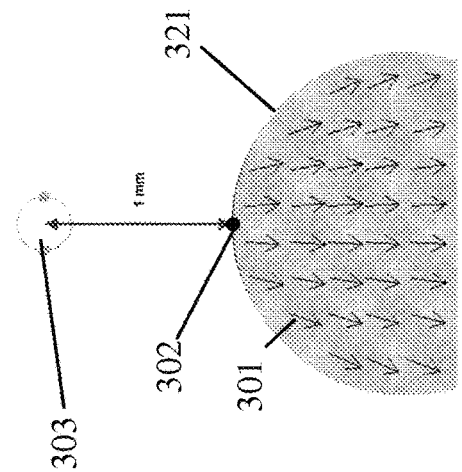
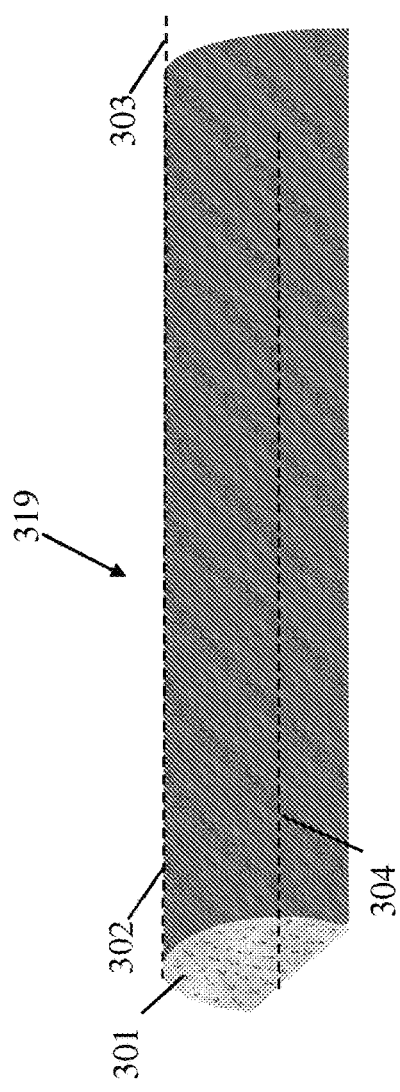
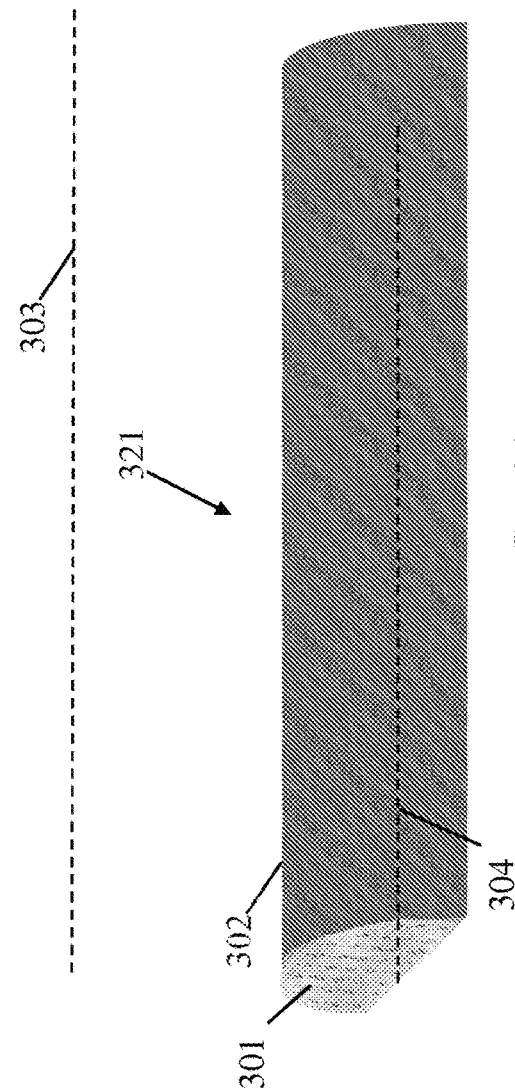

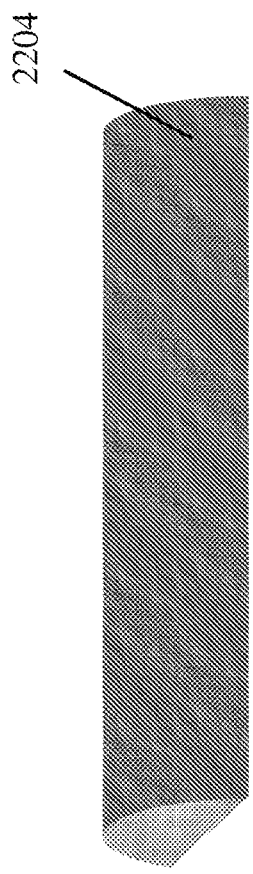
FIG. 22A
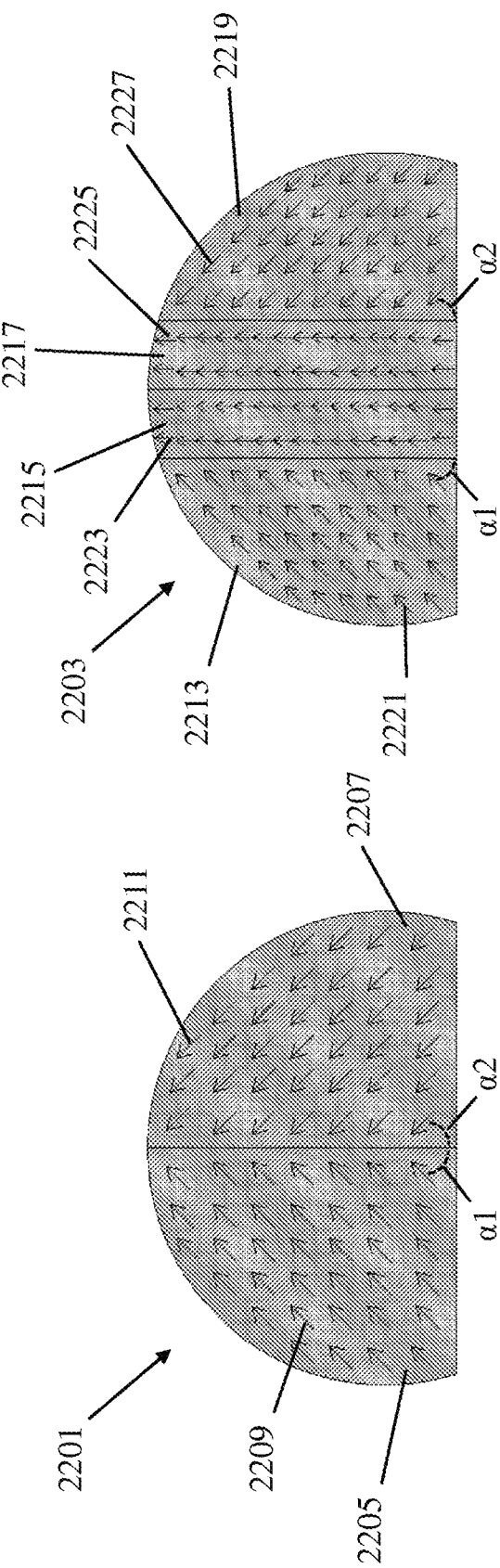
FIG. 22C
FIG. 22B

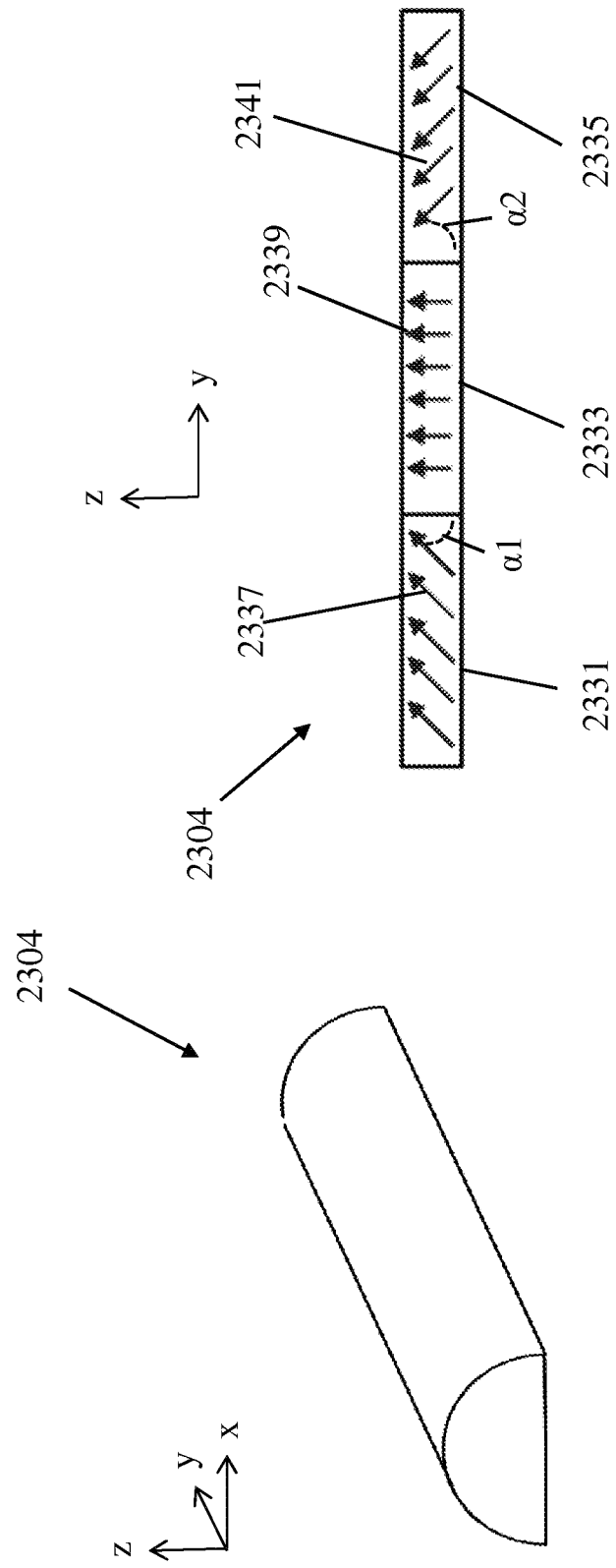

FISTULA FORMATION DEVICES AND METHODS THEREFOR

CROSS-REFERENCE TO RELATED APPLICATIONS

This application is a divisional of U.S. patent application Ser. No. 14/657,997, now U.S. Pat. No. 10,695,534, entitled "FISTULA FORMATION DEVICES AND METHODS THEREFOR," filed Mar. 13, 2015, which claims priority to U.S. Provisional Application Ser. No. 61/953,723, entitled "FISTULA FORMULATION DEVICES AND METHODS THEREFOR," filed on Mar. 14, 2014, the contents of which are hereby incorporated in their entireties.

FIELD

The current invention relates to devices and methods for forming a fistula. The devices and methods may be used to form a fistula between two blood vessels.

BACKGROUND OF THE INVENTION

A fistula is generally a passageway formed between two internal organs. Forming a fistula between two blood vessels can have one or more beneficial functions. For example, the formation of a fistula between an artery and a vein may provide access to the vasculature for hemodialysis patients. Specifically, forming a fistula between an artery and a vein allows blood to flow quickly between the vessels while bypassing the capillaries. In other instances, a fistula may be formed between two veins to form a veno-venous fistula. Generally, fistula formation requires surgical dissection of a target vein, and transecting and moving the vein for surgical anastomosis to the artery. It may therefore be useful to find improved ways to form a fistula between two blood vessels.

BRIEF SUMMARY OF THE INVENTION

Described here are devices, systems, and methods for forming a fistula. In some variations, the systems described here may comprise a first catheter and a second catheter. The first catheter may comprise one or more fistula-forming elements. The fistula-forming element may be any suitable structure, such as an electrode. Additionally or alternatively, the second catheter may comprise one or more fistula-forming elements. The first and second catheters may comprise one or more magnets, which may be used to move the first and second catheters in closer proximity to facilitate fistula formation and/or to assist in aligning the first and second catheters. In some variations, the magnets may have magnetization patterns such that the magnetic field generated by the magnets is locally concentrated. In some of these variations, the first catheter may comprise a first magnet comprising a plurality of magnetic domains each having a magnetic flux vector. The plurality of magnetic domains of the first magnet may be configured such that the magnetic flux vector of each magnetic domain intersects or passes through a common magnetic origin. In some of these variations, the second catheter may comprise a second magnet comprising a plurality of magnetic domains each having a magnetic flux vector. The plurality of magnetic domains of the second magnet may be configured such that the magnetic flux vector of each magnetic domain passes through a common magnetic origin.

In some variations of the systems described here, the system for creating a fistula between two vessels comprises a first catheter comprising a first magnet, and a second catheter comprising a second magnet, wherein at least one of the first and second catheters comprises a fistula-forming element, and wherein the first magnet is characterized by a first magnetization pattern comprising a first plurality of magnetic flux vectors, wherein each of the first plurality of magnetic flux vectors intersects a first magnetic origin. In some of these variations, the first magnet comprises a longitudinal axis, and the first magnetic origin comprises a first line oriented substantially parallel to the longitudinal axis of the first magnet. In some of these variations, the first magnet has an approximately D-shaped cross-section and a longitudinal apex, and the magnetic origin is offset from the longitudinal apex by between about 0.25 mm and about 0.5 mm. In some of these variations, the second magnet is characterized by a second magnetization pattern comprising a second plurality of magnetic flux vectors, wherein each of the second plurality of magnetic flux vectors intersects a second magnetic origin. In some of these variations, the first plurality of magnetic flux vectors is directed toward the first magnetic origin and the second plurality of magnetic flux vectors is directed away from the second magnetic origin. In some of these variations, the first magnetic origin and the second magnetic origin at least partially overlap. In some of these variations, the second magnet comprises a longitudinal axis, and the second magnetic origin comprises a second line oriented substantially parallel to the longitudinal axis of the second magnet. In some of these variations, the first magnet comprises a longitudinal axis, and the first magnetic origin comprises a first line oriented substantially perpendicular to the longitudinal axis. In some variations, the first and second magnets are configured such that when the rotational misalignment between the first and second magnets is greater than about 35 degrees, the attractive force between the first and second magnets is less than about 50 percent of the attractive force when the rotational misalignment between the first and second magnets is zero. In some of these variations, the fistula-forming element is an electrode.

In some variations of the systems described here, the system for creating a fistula between two vessels comprises a first catheter comprising a first magnet characterized at least partially with a first plurality of magnetic flux vectors and a second catheter comprising a second magnet, wherein at least one of the first and second catheters comprises a fistula-forming element. In some of these variations, a first portion of the first plurality of magnetic flux vectors is oriented in a first direction and a second portion of the first plurality of magnetic flux vectors is oriented in a second direction different from the first direction. In some of these variations, the second magnet is characterized at least partially with a second plurality of magnetic flux vectors, wherein a first portion of the second plurality of magnetic flux vectors is oriented in a third direction and a second portion of the second plurality of magnetic flux vectors is oriented in a fourth direction different from the third direction. In some of these variations, the first and second portions of the first plurality of magnetic flux vectors are directed toward a first common locus, and the first and second portions of the second plurality of magnetic flux vectors are directed away from a second common locus. In some of these variations, the first common locus and the second common locus at least partially overlap. In some of these variations, the fistula-forming element is an electrode.

In some variations of the methods described here, the method of forming a fistula between a first blood vessel and a second blood vessel of a patient comprises advancing a first catheter into the first blood vessel, wherein the first catheter comprises first magnet, advancing a second catheter into the second blood vessel, wherein the second catheter comprises a second magnet, and wherein at least one of the first and second catheters comprises a fistula-forming element, moving the first catheter toward the second catheter using the magnetic field produced by the first magnet and second magnet, and forming a fistula with the fistula-forming element, and wherein the first magnet is characterized by a first magnetization pattern comprising a first plurality of magnetic flux vectors, wherein each of the first plurality of magnetic flux vectors intersects a first magnetic origin, wherein the second magnet is characterized by a second magnetization pattern comprising a second plurality of magnetic flux vectors, wherein each of the second plurality of magnetic flux vectors intersects a second magnetic origin. In some of these variations, the first magnet comprises a first longitudinal axis and the second magnet comprises a second longitudinal axis, and the first magnetic origin comprises a first line oriented substantially parallel to the first longitudinal axis, and the second magnetic origin comprises a second line oriented substantially parallel to the second longitudinal axis. In some of these variations, the fistula-forming element is an electrode, and forming the fistula with the fistula-forming element comprises ablating tissue with the electrode. In some of these variations, the first blood vessel is a vein and the second blood vessel is an artery.

BRIEF DESCRIPTION OF THE DRAWINGS

FIGS. 3A-11B are illustrative depictions of variations of magnets each having an approximately D-shaped transverse cross-section and a magnetization pattern suitable for use with the catheters described here.

FIG. 22A is an illustrative depiction of a magnet having an approximately D-shaped transverse cross-section. FIGS. 22B and 22C are illustrative depictions of transverse cross-sections of variations of the magnet depicted in FIG. 22A having magnetization patterns suitable for use with the catheters described here.

FIG. 23A is an illustrative depiction of a magnet having an approximately D-shaped transverse cross-section. FIG. 23B is an illustrative depiction of a longitudinal cross-section of the magnet depicted in FIG. 23A having a magnetization pattern suitable for use with the catheters described here.

DETAILED DESCRIPTION OF THE INVENTION

Figure 1:
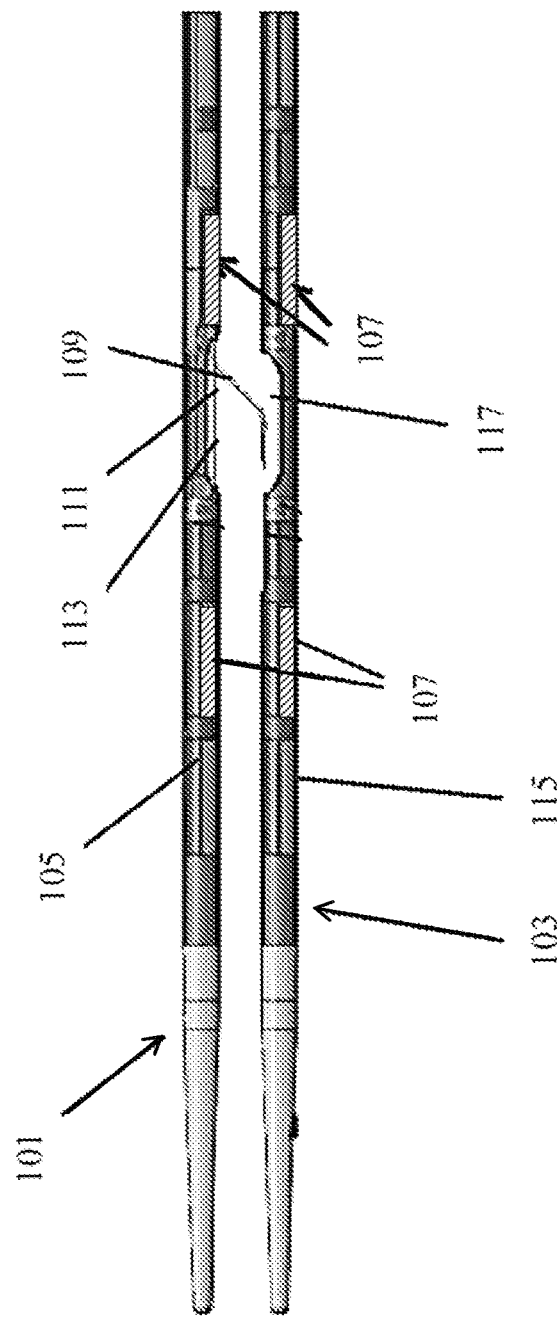
FIG. 1 is an illustrative depiction of a variation of a system described here comprising a first catheter and a second catheter.

Generally described here are systems, devices, and methods for forming a fistula between blood vessels. The fistula may be, for example, an arteriovenous fistula between an artery and a vein, or a veno-venous fistula between two veins. Generally, to form a fistula between two blood vessels, one or more catheters may be advanced in a minimally invasive fashion through the vasculature to a target fistula formation site. Typically, a catheter may be placed in each of the two blood vessels, such that a first catheter may be positioned in a first blood vessel and a second catheter may be positioned in a second blood vessel. Accordingly, the systems described here may comprise a first catheter and a second catheter.

The first and second catheters may each have one or more magnets, which may be configured to aid in positioning and/or alignment of the catheters. For example, in some instances the first catheter may comprise one or more magnets which may be attracted to one or more magnets of the second catheter, such that the magnets on the first and second catheters may act to pull the first and second catheters toward each other and/or act to rotate the first and second catheters into rotational alignment. In some variations, the magnets may have magnetization patterns generating non-uniform magnetic fields of focused magnetic strength. In some of these variations, the magnetization patterns may be configured to generate magnetic fields having the greatest magnetic flux density or strength at a location between the first and second catheters when the catheters are positioned in two blood vessels at a target fistula formation site.

Devices

Catheters

As mentioned above, the systems described here typically comprise a first catheter and a second catheter. Any suitable catheter or catheters may be used with the systems described here to form the fistulas using the methods described here. For example, in some variations the system may comprise one or more of the catheters described in U.S. patent application Ser. No. 13/298,169, filed on Nov. 16, 2011 and titled "DEVICES AND METHODS FOR FORMING A FISTULA," the contents of which are hereby incorporated by reference in their entirety. Generally, each catheter may have a proximal end, a distal end, and an intermediate portion connecting the proximal and distal ends. The proximal end may comprise one or more adaptors or handles, which may be utilized to help aid in advancement, positioning, and/or control of the catheter within the vasculature, and may further be used to actuate one or more components of the catheter and/or introduce one or more fluids or substances into and/or through the catheter. The catheter may comprise one or more elements that may aid in fistula formation. For example, one or more portions (e.g., the distal end and/or the intermediate portion) of the catheter may comprise one or more alignment elements, such as magnets, that may help to align the catheter with another catheter positioned in a related blood vessel, and/or help to bring the catheters into closer approximation, as will be described in more detail below. As the catheters are brought into closer approximation, the blood vessels within which the catheters are positioned may be brought into closer approximation, which may aid in fistula formation. Additionally or alternatively, one or more portions (e.g., the distal end and/or an intermediate portion) of the catheter may comprise one or more mechanisms for forming a fistula.

The catheters may additionally comprise one or more lumens or passageways extending at least partially along or through the catheter, but need not comprise these lumens or passageways. The lumens may be used to pass one or more guidewires, one or more drugs or fluids (e.g., contrast agents, perfusion fluids), combinations thereof, or the like at least partially along or through the catheter. The distal tip of the catheter may be configured to aid in advancement of the catheter and/or configured to be atraumatic. In some variations, the tip may comprise one or more rapid exchange portions or other lumens for advancement of the catheter over a guidewire. In still other variations, the tip portion may have a guidewire attached to or otherwise integrally formed with the catheter.

Additionally, in some variations the catheters may further comprise one or more external expandable elements (e.g., a balloon, expandable cage, mesh, or the like) that may help position a catheter within a blood vessel, but need not comprise one or more external expandable elements. Additionally or alternatively, the one or more expandable elements may affect the flow of blood through one or more blood vessels (e.g., by temporarily occluding blood flow through the blood vessel, dilating one or more portions of a blood vessel, constricting one or more portions of a blood vessel, or the like). In some instances, one or more expandable elements may act to temporarily anchor a portion of the catheter relative to a blood vessel. In variations in which a catheter comprises one or more shape-changing elements, as will be described in more detail below, the use of an expandable element to temporarily anchor a portion of the catheter relative to a blood vessel may aid in altering the shape of the catheter. It should be appreciated that the catheters described here may have any combination of the aforementioned elements.

FIG. 1 shows an illustrative variation of a catheter system that may be used to form a fistula between two vessels. As shown there, the system may comprise a first catheter (101) and a second catheter (103). The first catheter (101) may comprise a catheter body (105), one or more magnets (107), and a fistula-forming element (109) which may be activated to form a fistula. In some variations, the fistula-forming element (109) may be advanced within the catheter body (105) to project out of an opening (111) in the catheter body (105). In some variations, the first catheter (101) may comprise a housing (113), which may help protect other components of the first catheter (101) during fistula formation. For example, when the fistula-forming element (109) comprises an electrode configured to ablate tissue, the housing (113) may comprise one or more insulating materials which may shield or otherwise protect one or more components of the first catheter (101) from heat that may be generated by the electrode during use.

As shown in FIG. 1, a second catheter (103) may also comprise a catheter body (115) and one or more magnets (107). In variations in which the first catheter (101) comprises a fistula-forming element (109) configured to project out of the catheter body (105) of the first catheter (101), such as the variation depicted in FIG. 1, the catheter body (115) of the second catheter (103) may comprise a recess (117) therein, which may be configured to receive the fistula-forming element (109) as it passes through tissue during fistula formation. In some of these variations, the recess (117) may be coated by an insulating material (not shown), which may be configured to protect one or more components of the second catheter (103) from being damaged by the fistula-forming element (109) (e.g., the insulating material may shield one or more components of the second catheter (103) from heat that may be generated by the fistula-forming element (109)). While the second catheter (103) is shown in FIG. 1 as having a recess (117), it should also be appreciated that in some variations the second catheter (103) may not comprise a recess (117). In some variations, the second catheter may comprise a fistula-forming element (not shown) such that the first catheter (101) and/or the second catheter (103) comprises a fistula-forming element, as will be described in detail below.

Fistula-Forming Elements

As mentioned above, the catheters described here may comprise one or more elements for forming a fistula. The fistula-forming element may comprise any element capable of forming a fistula between two vessels, such as those elements described in U.S. patent application Ser. No. 13/298,169, which was previously incorporated by reference in its entirety. For example, the fistula-forming element may comprise one or more electrical mechanisms (e.g., electrodes or electrocautery mechanisms). A catheter may have any suitable number (e.g., zero, one, two, three, or four or more) and combination of these fistula-forming elements. The fistula-forming elements may be located in or on any suitable portion of the catheter (e.g., the distal end, an intermediate portion, or combinations thereof). In variations in which a catheter comprises two or more fistula-forming elements, multiple fistula-forming elements may be used to create multiple fistulas, either simultaneously or sequentially. In other variations, multiple fistula-forming elements may interact to form a single fistula.

In variations in which a system comprising multiple catheters is used to create a fistula between two blood vessels, each catheter may comprise a fistula-forming element, but need not. Indeed, in some of these variations, only one catheter may comprise a fistula-forming element. In some of these instances, a second catheter that lacks a fistula-forming element may still help align the catheters and/or bring the blood vessels into apposition, but might not directly contribute to tissue removal. In variations in which multiple catheters each comprise a fistula-forming element, the catheters may have complementary fistula-forming elements. For example, in variations in which two or more catheters each comprise an electrode, one catheter may comprise an electrode that acts as an active electrode, while another catheter may comprise an electrode that acts as a passive or ground electrode.

In some variations of the catheters described here, a catheter may comprise one or more electrodes for use in forming a fistula. Such an electrode may be used to ablate or otherwise remove the tissue in contact with the electrode in order to form the fistula. If a fistula-forming element comprises an electrode, the electrode may, for example, be configured as described in U.S. patent application Ser. No. 13/298,169, which was previously incorporated by reference in its entirety.

In the embodiment shown in FIG. 1, the fistula-forming element (109) of the first catheter (101) comprises an electrode. The electrode may be selectively moved from a position in which the electrode is retained or otherwise held in the catheter body (105) to a position in which the electrode extends away from the catheter body (105) (e.g., through the opening (111)), and the electrode may also be selectively moved back to a retracted/low-profile position (either the same position as the previous retracted position, or a different position) following ablation of tissue. This may allow the electrode to be maintained in a low-profile configuration during positioning of the catheter. In some variations, the electrode may be biased toward an extended position when not otherwise restrained by the catheter body (105).

Magnets

As mentioned above, the first and second catheters of the systems described here may comprise one or more magnets. Generally, the magnets may be configured to be attracted to one or more magnetic fields (e.g., produced by one or more magnets of another catheter). The magnets may help to align or otherwise reposition the catheters when placed in the vasculature. In some instances, a system may comprise first and second catheters each having one or more magnets, such that magnets of the first catheter may be attracted to magnets of the second catheter to bring the catheters in closer approximation. In other instances, one or more magnets may help to ensure that one or more catheters are in proper axial and/or rotational alignment relative to another catheter or catheters, such as described in further detail in U.S. patent application Ser. No. 13/298,169, which was previously incorporated by reference in its entirety. Such axial and/or rotational alignment of catheters may also facilitate alignment of one or more fistula-forming elements relative to a target fistula-formation site.

The magnets described here may be permanent magnets comprising one or more hard magnetic materials, such as but not limited to alloys of rare earth elements (e.g., samarium-cobalt magnets or neodymium magnets, such as N52 magnets) or alnico. In some variations, the magnets may comprise anisotropic magnets; in other variations, the magnets may comprise isotropic magnetics. In some variations, the magnets may be formed from compressed powder, as will be described in more detail below. In some variations, a portion of the magnets (e.g., a permeable backing) may comprise one or more soft magnetic materials, such as but not limited to iron, cobalt, nickel, or ferrite.

It should be appreciated that while the systems primarily described here comprise a first catheter and a second catheter each comprising one or more permanent magnets, in other variations either the first or second catheter may comprise ferromagnetic elements (i.e., elements attracted to but not generating a permanent magnetic field). For example, in some variations, the first catheter may include only one or more ferromagnetic elements while the second catheter comprises one or more permanent magnets. In other variations, the second catheter may include only one or more ferromagnetic elements while the first catheter comprises one or more permanent magnets. However, in other variations, one or both of the first and second catheters may include any suitable combination of ferromagnetic, permanent, and/or other suitable kinds of magnets.

In variations in which the catheters of the systems described here comprise one or more magnets, each catheter may comprise any number of individual magnets (e.g., one, two, three, four, five, six, seven, or eight or more, etc.). In variations in which a catheter comprises a plurality of magnets, these magnets may be grouped into one or more magnet arrays. The magnets may be located inside and/or outside of a catheter body. The magnets may be positioned anywhere along the length of the catheter. In some variations in which the system comprises a first catheter having a fistula-forming element (such as the first catheter (101) shown in FIG. 1), the first catheter may comprise one or more magnets proximal to a fistula-forming element. Additionally or alternatively, the first catheter may comprise one or more magnets distal to a fistula-forming element. In some variations in which a system comprises a second catheter comprising a fistula-forming element, the second catheter may comprise one or more magnets proximal to the fistula-forming element. Additionally or alternatively, in variations in which the second catheter comprises a fistula-forming element, the second catheter may comprise one or more magnets distal to the fistula-forming element. In variations in which both the first and second catheters comprise one or more magnets, each magnet or array in the first catheter may be configured to align with one or more magnets in a second catheter. Each magnet may be fixed in or on a catheter by any suitable method. For example, in some variations one or more magnets may be embedded in, adhered to, or friction-fit within a catheter.

Generally, the dimensions of the magnets may be constrained by the size of the catheters carrying the magnets, which in turn may be constrained by the anatomical dimensions of the selected blood vessels through which the catheters described here may be advanced. For example, if the catheter is to be advanced through a blood vessel having an internal diameter of about 3 mm, it may be desirable to configure any magnet to be less than about 3 mm at the widest part of its cross-section, to reduce the risk of injury to vessel walls during advancement and manipulation of the catheter. Each magnet may have any suitable length (e.g., about 5 mm, about 10 mm, about 15 mm, about 20 mm, or the like), although it should be appreciated that in some instances longer magnets may limit the flexibility of the catheter to maneuver through tissue.

In variations in which two catheters each comprise one or more magnets, the magnets of the catheters may produce an attractive force between the catheters, which may act to pull the catheters into closer approximation. Once the first and second catheters have been positioned, the attractive force may also act to maintain the relative positions of the catheters. When the first and second catheters are placed in respective blood vessels, however, tissue positioned between the blood vessels and/or limited compliance of the blood vessels may limit the extent to which the magnets of the first and second catheters bring the first and second catheters toward each other.

"Focused" Magnets

The extent to which the first and second catheters may be brought toward and/or rotationally aligned with each other may be improved by utilizing magnets having particular magnetic fields of focused strength. Such "focused" magnets have a magnetic field with at least one region in which magnetic strength is higher than surrounding regions, as compared to "non-focused" magnets (described in more detail below). In particular, the magnetic field patterns of the respective magnets on the first and second catheters may be designedly focused in order to urge the first and second catheters toward a desired arrangement with one another, with more force than that provided by magnets with uniform magnetic fields. For example, when the first and second catheters are within respective blood vessels near a target fistula formation site, the magnetic field strength of the focused magnets may be focused at a common location between the first and second catheters, thereby urging the first and second catheters into closer approximation with an increased attractive force as compared to non-focused magnets of the same size. Thus, the catheters may be better able to displace tissue between the blood vessels or overcome limited vessel compliance in order to help the first and second catheters move toward each other.

Because the catheters described herein may be advanced into the body, the patient's anatomy and other factors may place constraints on the dimensions of the catheters and the magnets that ordinarily would limit the amount of attractive force provided by magnets on the catheters. Accordingly, in instances in which the size of catheters and the magnets are physically limited to a particular size, the inclusion of focused magnets having focused magnetic fields may facilitate an additional increase in attractive force between two catheters comprising such magnets, without exceeding dimensional constraints. This may, for example, allow the catheters to overcome additional compliance and/or resistance (e.g., due to tissue between the vessels) to help bring the catheters and/or blood vessels into apposition. Alternatively, focused magnets having focused magnetic fields may allow the catheter size to be decreased while maintaining a certain attractive force between the catheters. For example, in some instances, the catheter size may be able to be decreased from 5 Fr to 4 Fr while maintaining the same attractive force between the catheters; in other instances, the catheter size may be able to be decreased from 6 Fr to 5 Fr while maintaining the same attractive force between the catheters.

Figure 2B:
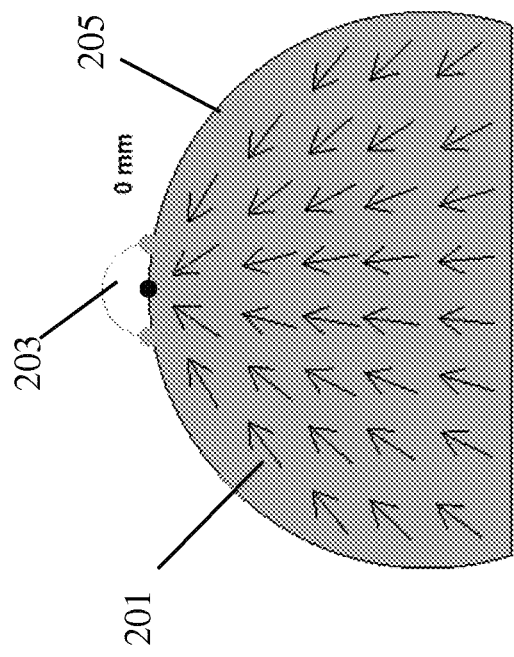
FIG. 2B is an illustrative depiction of a magnet having an approximately D-shaped transverse cross-section and a magnet having non-parallel magnetic flux vectors.
Figure 2A:
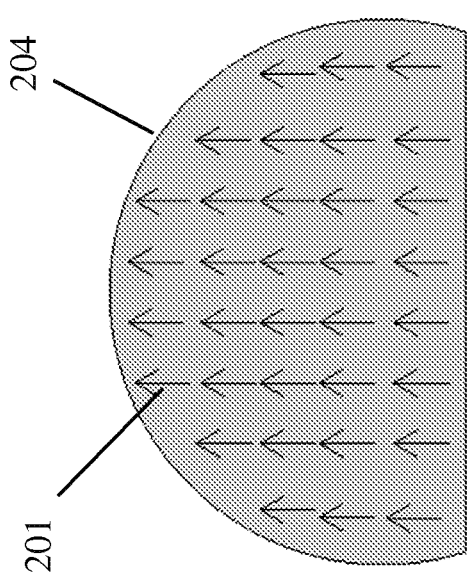
FIG. 2A is an illustrative depiction of a magnet having an approximately D-shaped transverse cross-section and a magnetization pattern with parallel magnetic flux vectors.

Compared to a non-focused magnet, a focused magnet may create a magnetic field of focused strength as a result of having a specialized magnetization pattern. FIG. 2A illustrates the magnetization pattern of a cross-section of an exemplary non-focused magnet (204), and FIG. 2B illustrates the specialized magnetization pattern of a cross-section of an exemplary focused magnet (205). Each magnet includes a plurality of regions, or magnetic domains. Each magnetic domain has a uniform magnetization within itself, and a respective polarity direction that is represented by a magnetic flux vector (201). The difference between a non-focused magnet and a focused magnet is illustrated by the different magnetization pattern of their magnetic domains. As shown in FIG. 2A, a non-focused magnet (204) has a magnetization pattern characterized with parallel magnetic flux vectors (201) that are oriented in the same direction (shown in FIG. 2A as directed upward). In contrast, as shown in FIG. 2B, a focused magnet (205) has a magnetization pattern characterized with non-parallel magnetic flux vectors (201) forming a specialized magnetization pattern in which each magnetic flux vector (201) intersects or passes through a particular common location or common locus called the magnetic origin (203). Put another way, a focused magnet has a magnetic origin located a measurable distance (i.e., a non-infinite distance) from the magnet (hereinafter referred to as "magnetization radius") where magnetic flux vectors (201) meet, while a non-focused magnet has a magnetic origin located an infinite distance away from the magnet (i.e., a non-focused magnet has a magnetization radius of infinity). Accordingly, the magnetization pattern concentrates or focuses magnetic flux at the magnetic origin, such that the magnetic field strength of the magnet is maximum at the magnetic origin (203). In other words, a focused magnet with such a focused magnetic field generates a greater magnetic flux density, or greater magnetic force, at the magnetic origin than that otherwise generated by a non-focused magnet of similar dimensions and material type.

Figure 3A:
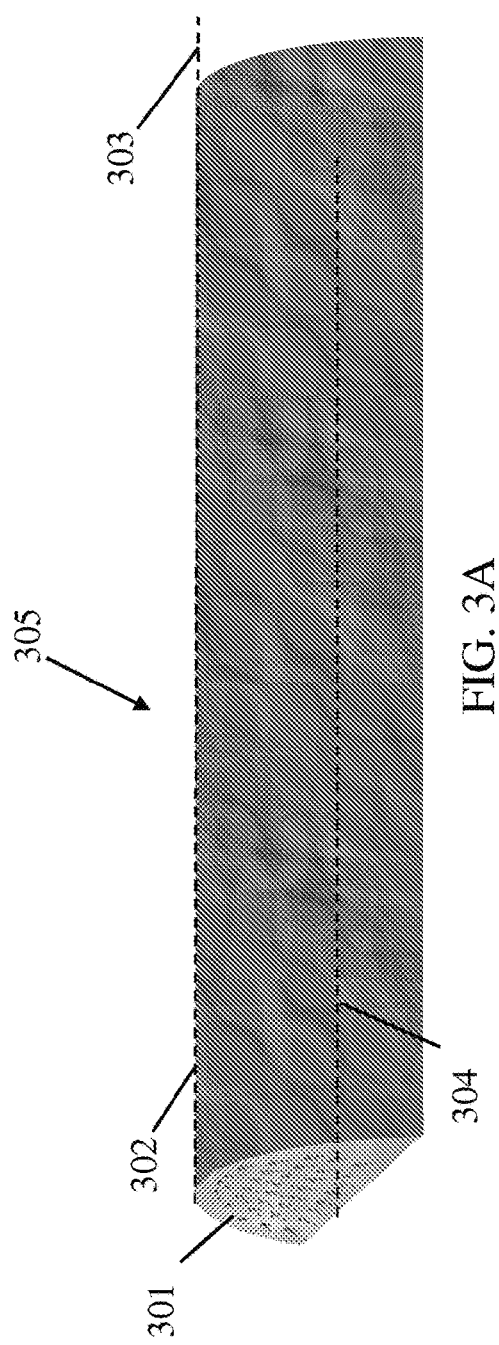
Figure 3B:
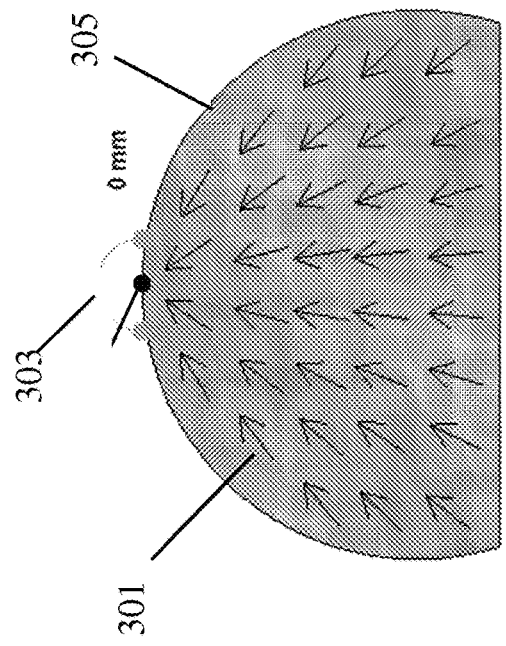
Figure 4A:
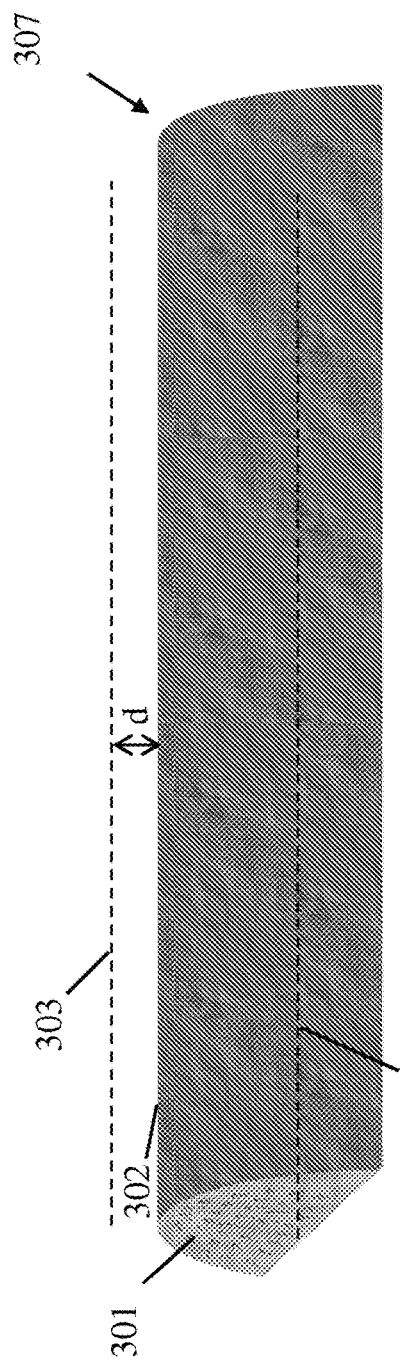
Figure 4B:
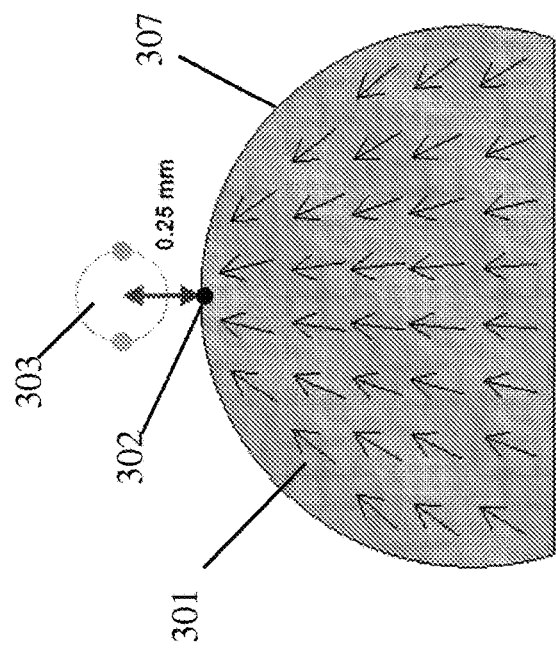
Figure 5A:
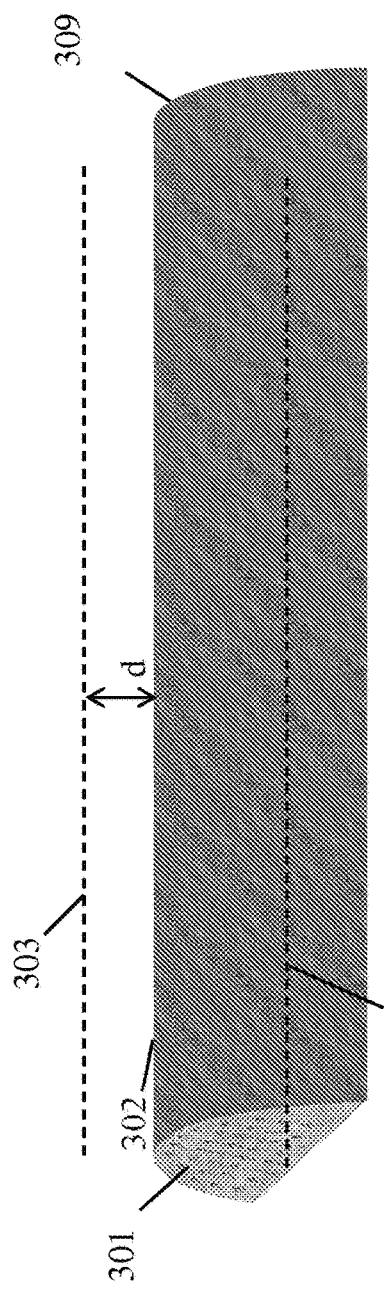
Figure 5B:
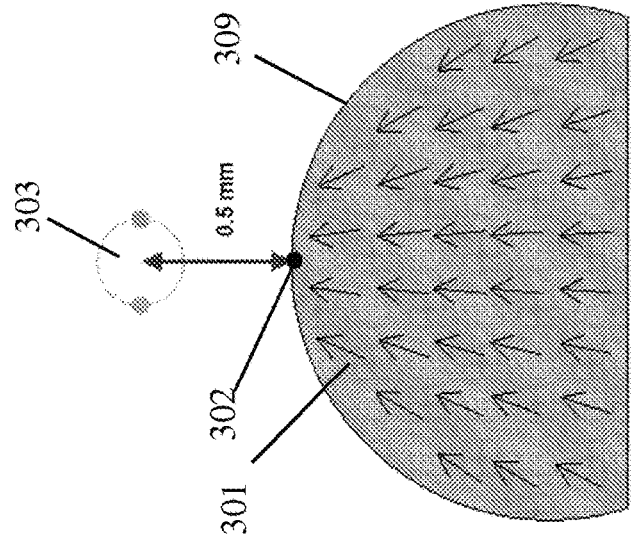
Figures 9A, 9B:
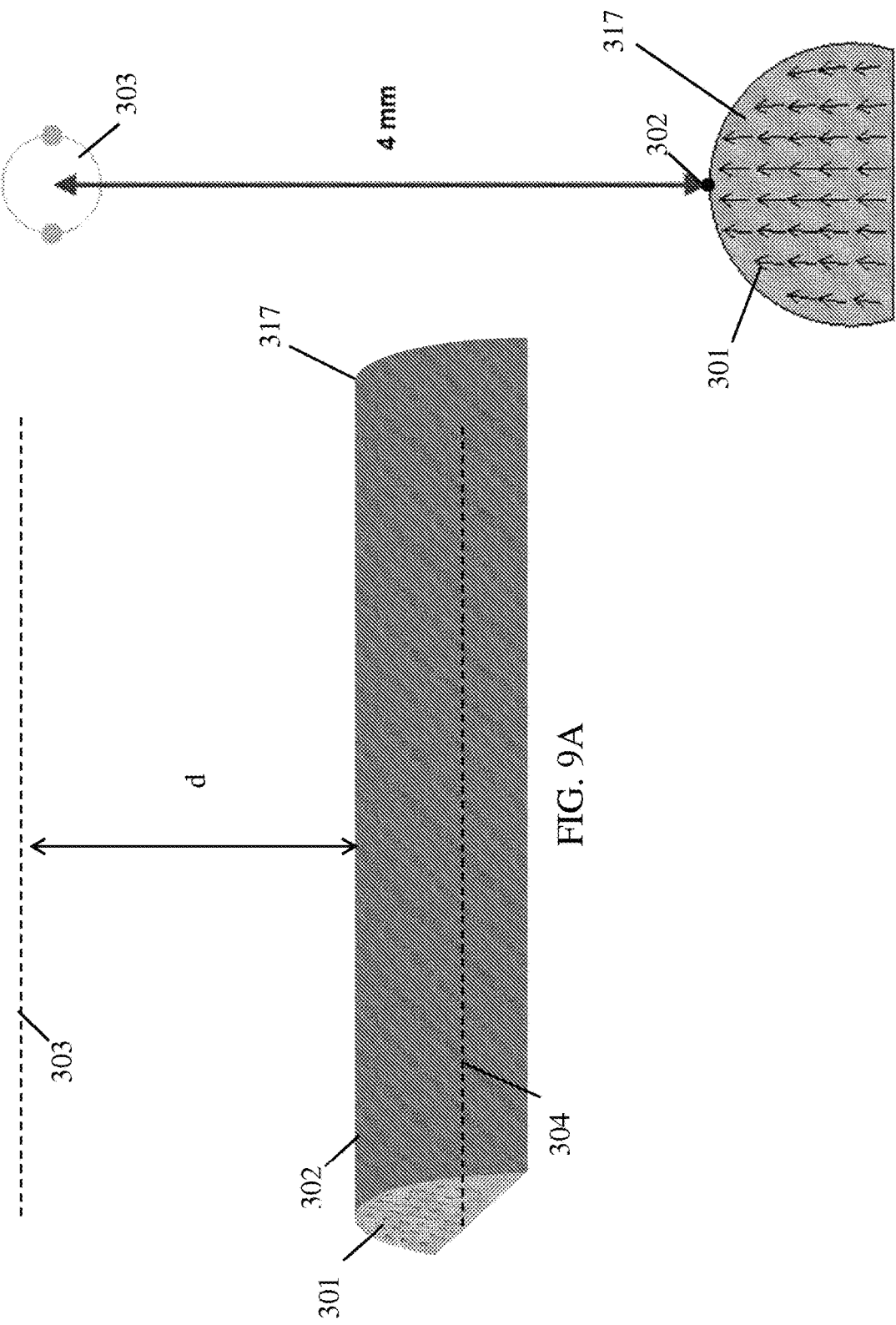

In some variations, as shown for example in FIGS. 3A and 3B, a focused magnet may have a longitudinal magnetic origin (shown as line (303) in FIG. 3A) in the form of a line parallel to a longitudinal axis of the magnet (shown as line (304) in FIG. 3A). For example, a focused magnet may have a longitudinal magnetic origin in the form of a line translated from the longitudinal axis of the magnet (i.e., oriented parallel to and located offset from the longitudinal axis of the magnet). In these variations, as shown in FIGS. 3A-11B (discussed in more detail below), the magnetization pattern of each transverse cross-section of the magnet may include magnetic flux vectors that commonly pass through a single point along the longitudinal magnetic origin, where that single point is in the plane of the transverse cross-section. In other words, the magnetic field of each transverse "slice" of the focused magnet may be represented by a respective set of magnetic flux vectors that intersect at a respective single common point, and the series of common points along all "slices" form the longitudinal magnetic origin. As such, the magnetic force produced along the longitudinal magnetic origin of a focused magnet is greater than the magnetic force produced by a non-focused magnet. In some of these variations, the line may be located along a central longitudinal plane of the magnet.

FIGS. 3A-11B depict exemplary variations of focused magnets with longitudinal magnetic origins. Each of FIGS. 3A-11A depicts a focused magnet having an approximately D-shaped transverse cross-section (shown in FIGS. 3B-11B, respectively) and a longitudinal apex (302) that extends longitudinally along the apex of convexity of the magnet, substantially parallel to longitudinal axis (304). Each of the magnets of FIGS. 3A-11B comprises a plurality of magnetic domains, where each magnetic domain may be represented by a respective magnetic flux vector (each represented by an arrow (301)). When fully extended within its plane, each magnetic flux vector (301) passes through a point on the longitudinal magnetic origin (303). In some variations, as shown in FIGS. 3A-11B, a focused magnet may have a longitudinal magnetic origin (303) that is translated or offset by any suitable distance (d) (not labeled in FIGS. 3A and 3B) from the longitudinal apex (302) of the magnet (i.e., offset by the magnetization radius). In some variations, the magnetization radius may be about 0 mm to about 6 mm, about 0.1 mm to about 5 mm, about 0.2 mm to about 4 mm, about 0.3 mm to about 3 mm, about 0.4 mm to about 2 mm, about 0.5 mm to about 1 mm, or more than about 6 mm. Generally speaking, as the magnetization radius is increased and the magnetic origin is more distant from a focused magnet, the magnetic flux vectors of the magnet become less angled (i.e., become closer to approximating parallel orientations). For example, FIG. 3B depicts a transverse cross-section of a magnet (305) having a magnetization radius of about 0 mm (i.e., a longitudinal magnetic origin (depicted by circle (303)) located substantially incident or collinear with the longitudinal apex (302) of the magnet (305)). FIG. 4B depicts a transverse cross-section of a magnet (307) having a magnetization radius of about 0.25 mm (i.e., a longitudinal magnetic origin (303) located about 0.25 mm from the longitudinal apex (302) of the magnet (307)). FIG. 5B depicts a transverse cross-section of a magnet (309) having a magnetization radius of about 0.5 mm (i.e., a longitudinal magnetic origin (303) about 0.5 mm from the longitudinal apex (302) of the magnet (309)). FIG. 6B depicts a transverse cross-section of a magnet (311) having a magnetization radius of about 0.75 mm (i.e., a longitudinal magnetic origin (303) about 0.75 mm from the longitudinal apex (302) of the magnet (311)). FIG. 7B depicts a transverse cross-section of a magnet (313) having a magnetization radius of about 1 mm (i.e., a longitudinal magnetic origin (303) about 1 mm from the longitudinal apex (302) of the magnet (313)). FIG. 8B depicts a transverse cross-section of a magnet (315) having a magnetization radius of about 2 mm (i.e., a longitudinal magnetic origin (303) about 2 mm from the longitudinal apex (302) of the magnet (315)). FIG. 9B depicts a transverse cross-section of a magnet (317) having a magnetization radius of about 4 mm (i.e., a longitudinal magnetic origin (303) about 4 mm from the longitudinal apex (302) of the magnet (317)).

While FIGS. 3A-11B show magnets comprising a plurality of magnetic domains with magnetic flux vectors passing through and oriented toward the magnetic origin, in other variations, as shown for example in FIGS. 10A-10B and 11A-11B, the magnets may comprise a plurality of magnetic domains with magnetic flux vectors intersecting (when extended) the magnetic origin and oriented away from the magnetic origin. For example, FIG. 10B depicts a transverse cross-section of a magnet (319) having a magnetization radius of about 0 mm (i.e., a magnetic origin (303) located substantially incident or collinear with the longitudinal apex (302) of the magnet (319), where each magnetic flux vector (301) intersects the magnetic origin (303) and is oriented away from the magnetic origin (303). FIG. 11B depicts a transverse cross-section of a magnet (321) having a magnetization radius of about 1 mm (i.e., a magnetic origin (303) located about 1 mm from the longitudinal apex (302) of the magnet (321)), where each magnetic flux vector (301) intersects the magnetic origin (303) and is oriented away from the magnetic origin (303). Furthermore, while FIGS. 3B-11B depict a single transverse cross-section of each magnet, it should be appreciated that when the magnetic origin is a longitudinal magnetic origin, some or all transverse cross-sections of the magnet may have substantially similar magnetization patterns, such that the magnetic domains in at least some transverse cross-sections of the magnet are represented by substantially similar configurations of magnetic flux vectors.

Figure 12B:
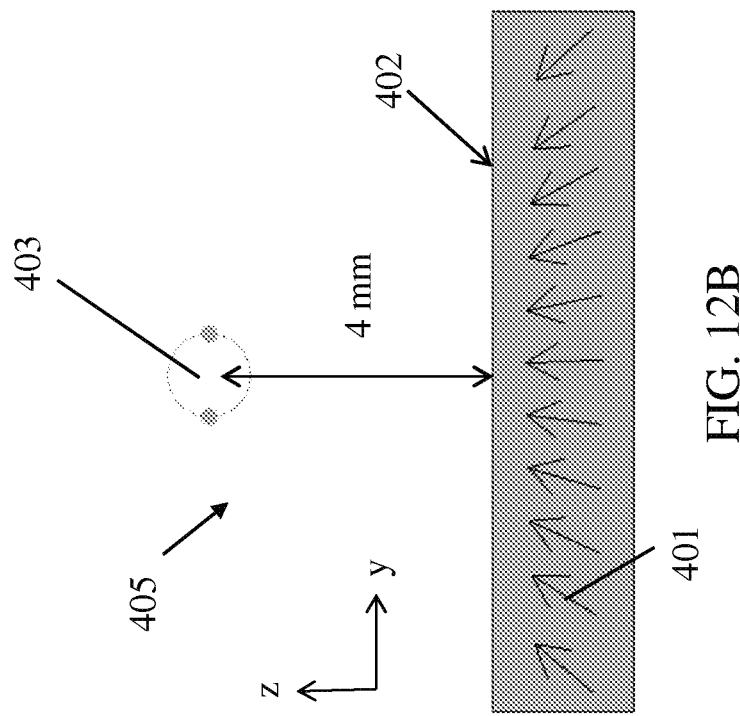
FIG. 12B is an illustrative depiction of a longitudinal cross-section of the magnet depicted in FIG. 12A having a magnetization pattern suitable for use with the catheters described here.
Figure 12A:
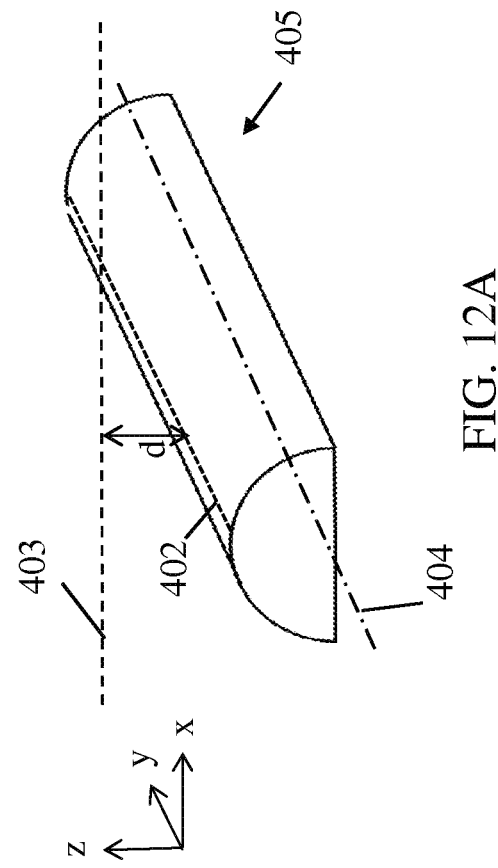
FIG. 12A is an illustrative depiction of a magnet having an approximately D-shaped transverse cross-section.

In other variations, as shown for example in FIG. 12A, a focused magnet may have a transverse magnetic origin (shown as line (403) in FIG. 3A) in the form of a line that is approximately perpendicular to a longitudinal axis (shown as line (403) in FIG. 12A). In these variations, as shown in FIG. 12B (discussed in more detail below), the magnetization pattern of each longitudinal cross-section of the magnet may include magnetic flux vectors that commonly pass through a single point along the transverse magnetic origin, where that single point is in the plane of the longitudinal cross-section. In other words, the magnetic field of each longitudinal "slice" of the focused magnet may be represented by a respective set of magnetic flux vectors that intersect at a respective single common point, and the series of common points along all "slices" form the transverse magnetic origin. As such, the magnetic force produced along the transverse magnetic origin of a focused magnet is greater than the magnetic force produced by a non-focused magnet of similar size and material type. In some of these variations, the line may be located along a central transverse plane of the magnet.

FIG. 12A depicts an exemplary variation of a focused magnet with a transverse magnetic origin (403). In particular, FIG. 12A depicts a focused magnet (405) having an approximately D-shaped transverse cross-section and a longitudinal apex (402) that extends longitudinally along the apex of convexity of the magnet (405). FIG. 12B depicts a longitudinal cross-sectional view of a focused magnet similar to that depicted in FIG. 12A, and a transverse magnetic origin (403). That is, the magnet (405) of FIG. 12B may comprise a plurality of magnetic domains, where each magnetic domain may be represented by a respective magnetic flux vector (each represented by an arrow (401)). When fully extended, each magnetic flux vector (401) passes through a point on the transverse magnetic origin (depicted by circle (403)). As shown in FIGS. 12A and 12B, the transverse magnetic origin (403) may be translated or offset by any suitable distance (d) from the longitudinal apex (402) of the magnet, such as about 0 mm to about 6 mm, about 0.1 mm to about 5 mm, about 0.2 mm to about 4 mm, about 0.3 mm to about 3 mm, about 0.4 mm to about 2 mm, about 0.5 mm to about 1 mm, or more than about 6 mm. For example, FIG. 12B depicts a transverse cross-section of a magnet (405) having a magnetic origin (depicted by circle (403)) located about 4 mm from the longitudinal apex (402) of the magnet (405). Generally speaking, as the magnetization radius is increased and the magnetic origin is more distant from a focused magnet, the magnetic flux vectors of the magnet become less angled (i.e., become closer to approximating parallel orientations).

While FIG. 12B depicts a magnet comprising a plurality of magnetic domains with magnetic flux vectors passing through and oriented toward the magnetic origin, in other variations, the magnets may comprise a plurality of magnetic domains with magnetic flux vectors intersecting (when extended) the magnetic origin and oriented away from the magnetic origin. Furthermore, while FIG. 12B depicts a single longitudinal cross-section of the magnet (405), it should be appreciated that when the magnetic origin comprises a transverse magnetic origin, some or all longitudinal cross-sections of the magnet may have the same magnetization pattern, such that the magnetic domains in at least some longitudinal cross-sections of the magnet are represented by the substantially similar configurations of magnetic flux vectors.

In yet other variations, a focused magnet may have a magnetic origin in the form of a single point. As such, the magnetic force produced at this point may be greater than the magnetic force produced by a non-focused magnet of similar size and material type. In these variations, each magnetic flux vector of the magnet may pass through the single magnetic origin point. In some of these variations, the single magnetic origin point may be located along a line formed by the intersection of a central transverse plane of the magnet and a central longitudinal plane of the magnet.

It should also be appreciated that while FIGS. 2A-11B depict magnets having approximately D-shaped transverse cross-sections, in other variations, the magnets may have other shapes. For example, in other variations the magnets may be cylindrical, semi-cylindrical, or have a cross-section that is C-shaped (i.e., a D-shape or semi-cylindrical shape comprising a channel on the flat surface), rectangular, square, triangular, trapezoidal, ovoid, elliptical, or an $n^{th}$-order polygon, or the like.

Figure 13C:
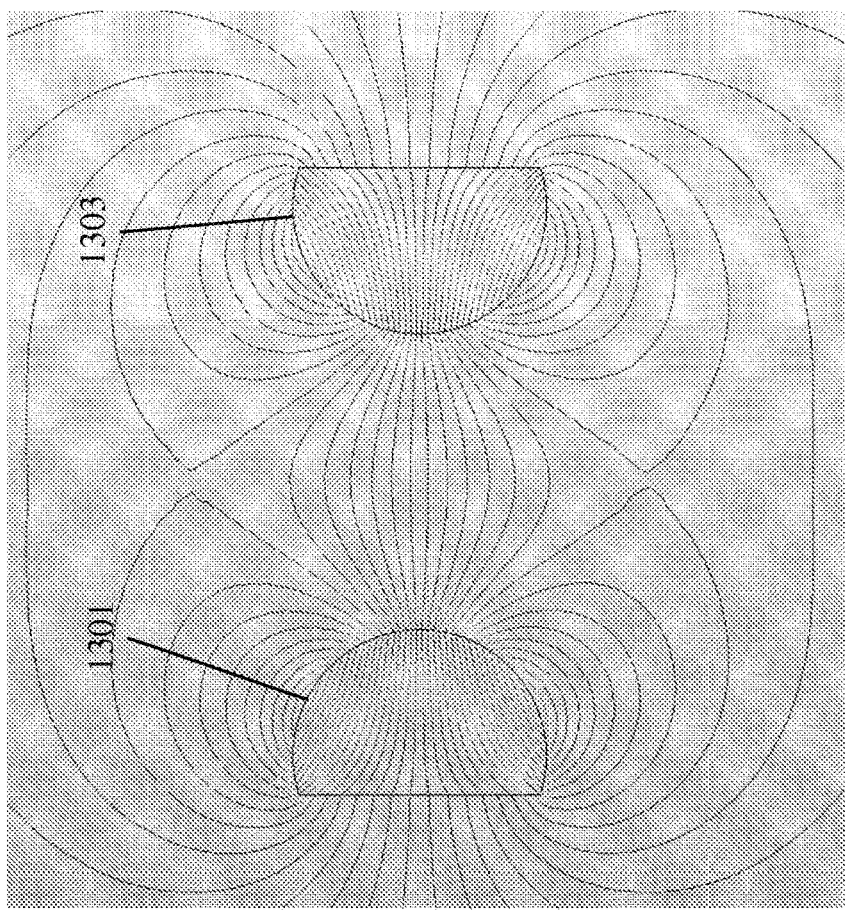
FIG. 13C is an illustrative depiction of a cross-section of the magnetic field produced by the magnet pair of FIG. 13B.
Figure 13A:
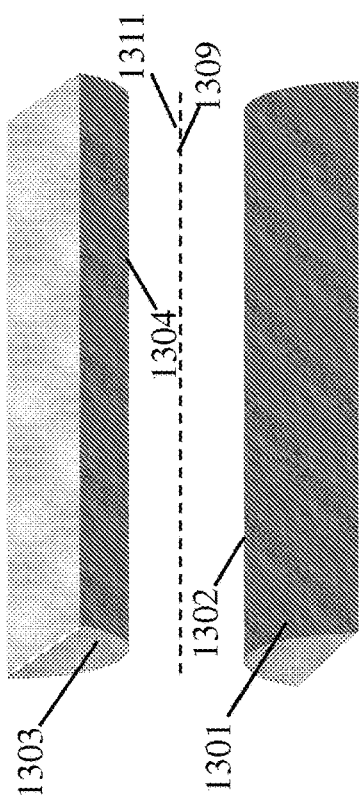
FIG. 13A is an illustrative depiction of a pair of magnets having approximately D-shaped transverse cross-sections.
Figure 13B:
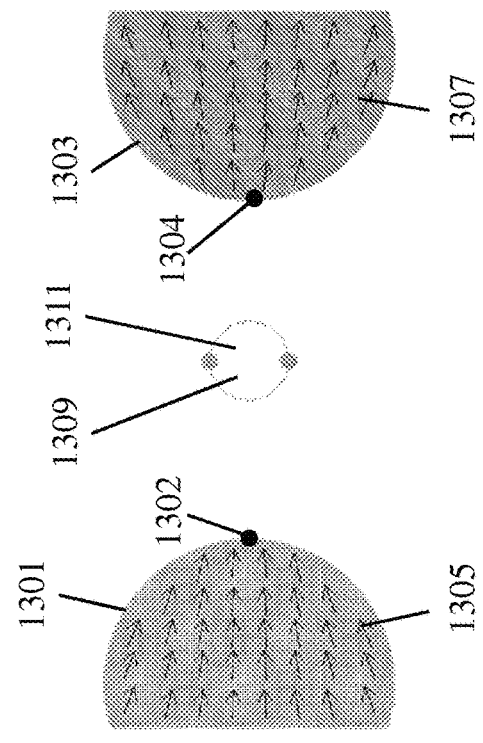
FIG. 13B is an illustrative depiction of a transverse cross-section of a variation of the magnet pair depicted in FIG. 13A having magnetization patterns suitable for use with the catheters described here.

In some variations, a first catheter may comprise a first magnet comprising a plurality of magnetic domains each having a magnetic flux vector oriented toward a magnetic origin, and a second catheter may comprise a second magnet comprising a plurality of magnetic domains each having a magnetic flux vector oriented away from a magnetic origin. For example, FIG. 13A depicts a first magnet (1301) having a longitudinal apex (1302) and second magnet (1303) having a longitudinal apex (1304). First magnet (1301) and second magnet (1303) may be located in first and second catheters (not shown), respectively. As shown in FIG. 13B, the first magnet (1301) may comprise a plurality of magnetic domains each having a magnetic flux vector (each depicted by an arrow (1305)) passing through and directed toward a longitudinal magnetic origin (1309) located about 1 mm from the longitudinal apex (1302) of the first magnet (1301). The second magnet (1303) may comprise a plurality of magnetic domains each having a magnetic flux vector (each depicted by an arrow (1307)) intersecting (when extended) a longitudinal magnetic origin (1311) and directed away from the longitudinal magnetic origin (1311), where the longitudinal magnetic origin (1311) is located about 1 mm from the longitudinal apex (1304) of the second magnet (1303).

When the first magnet (1301) and second magnet (1303) are positioned such that the convex side of the first magnet (1301) faces the convex side of the second magnet (1303) and the magnetic origins (1309) and (1311) are approaching the at least partial overlap or superposition depicted in FIGS. 13A and 13B, the magnetic field produced by the first magnet (1301) may attract the second magnet (1303) toward the first magnet (1301), while the magnetic field produced by the second magnet (1303) may in turn attract the first magnet (1301) toward the second magnet (1303). In some variations, the first magnet (1301) and the second magnet (1303) are configured such that their respective magnetic origins (1309) and (1311), respectively, are located in the center of the "air gap" distance between the magnets. FIG. 13C depicts the resulting magnetic field produced by the first magnet (1301) and second magnet (1303) when they are located about 2 mm away from each other. As illustrated in FIG. 13C, the greatest flux density is located in the area between the two magnets.

As described above, in some variations, a first catheter comprises a first focused magnet having a plurality of magnetic domains each having a magnetic flux vector oriented toward a magnetic origin, and a second catheter comprises a second focused magnet having a plurality of magnetic domains each having a magnetic flux vector oriented away from a magnetic origin. In such variations, the attractive force between the first magnet and the second magnet may in some instances be greater than the attractive force between two non-focused magnets (i.e., each having parallel magnetic flux vectors, with a magnetization radii of infinity). The increased attractive force between the first focused magnet and the second focused magnet may depend on the distance between the first and second focused magnets, the magnetic radii of the first and second focused magnets, and/or the rotational alignment of the first and second focused magnets.

Magnets—Attractive Force

Figure 14A:
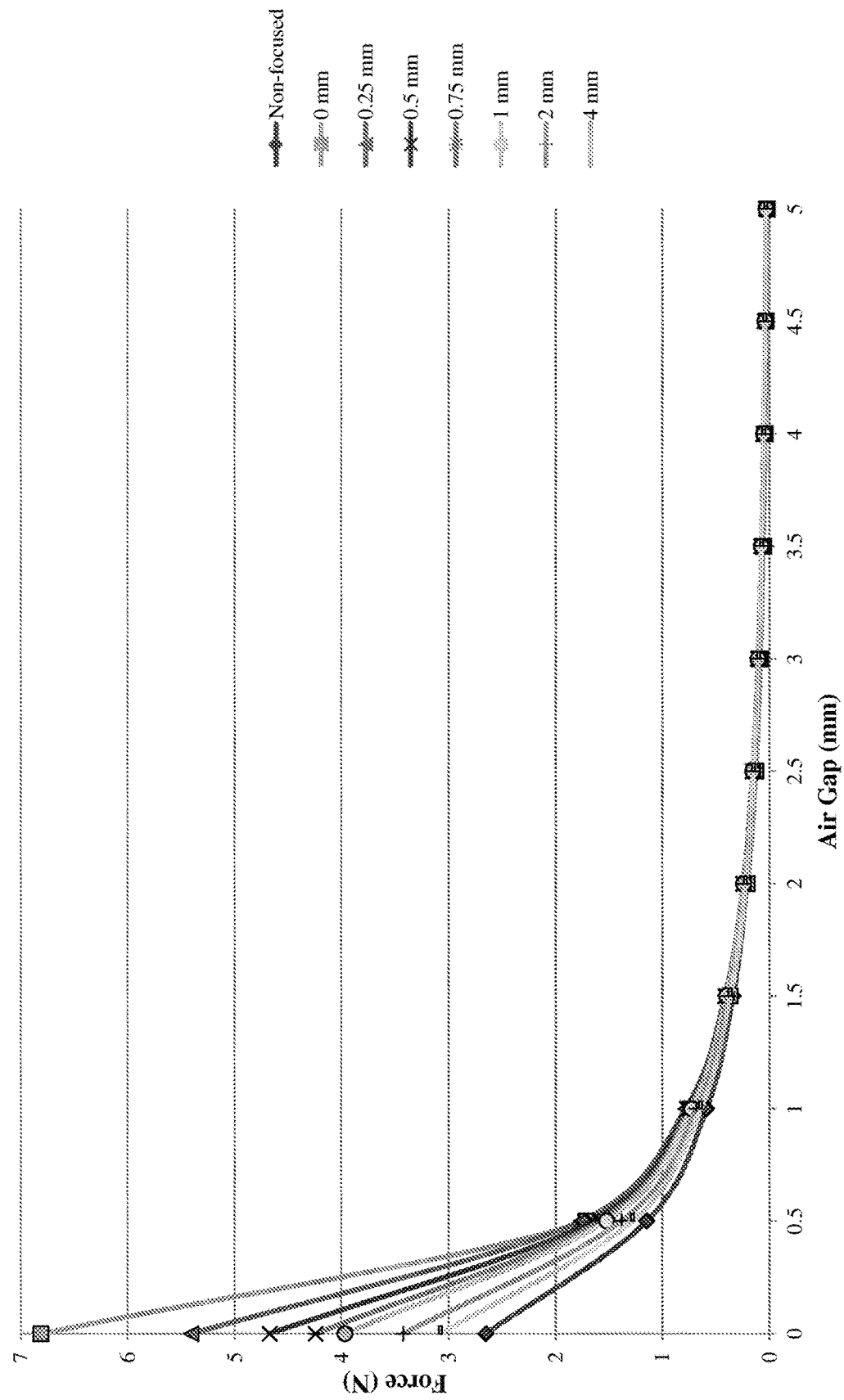
FIG. 14A depicts the attractive force between two magnets suitable for use with the catheters described here as a function of the distance between two magnets.
Figure 14B:
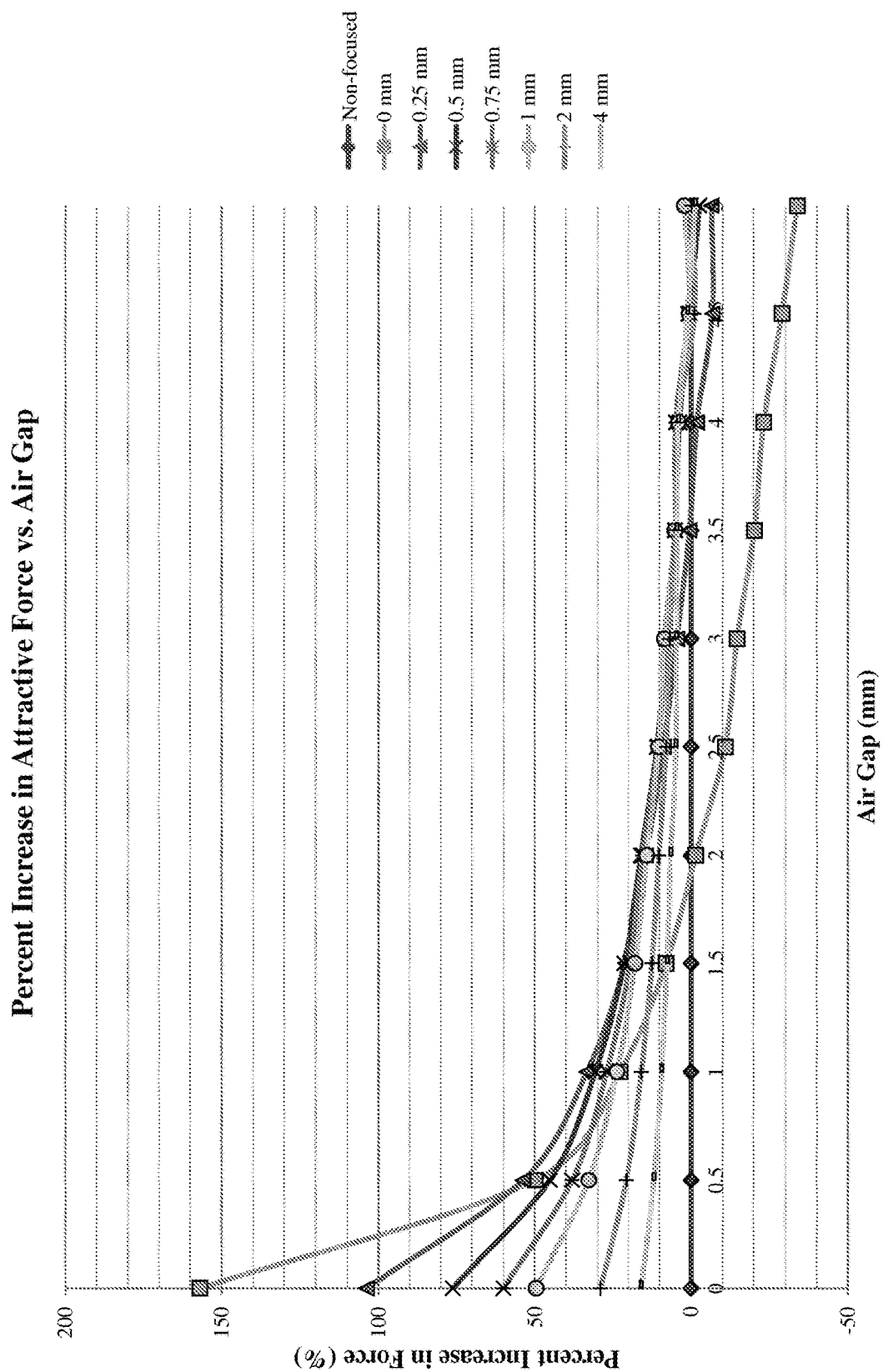
FIG. 14B depicts the percentage increase in the attractive force between the magnets of FIG. 14A as a function of the distance between the two magnets.

Different configurations of pairs of magnets may result in different amounts of attractive force. FIGS. 14A and 14B depict the attractive force between a pair of first and second magnets, as compared across different kinds of magnet pairs. In particular, FIG. 14A depicts the attractive force between first and second non-focused magnets as a function of the distance between the two magnets (the "air gap"). FIG. 14A also depicts the attractive force between a pair of first and second focused magnets as a function of the "air gap," for different pairs of focused magnets having a range of magnetic radii. The non-focused and focused magnets are N52 NdFeB magnets, each having a D-shaped transverse cross-section, a diameter of 0.0675 inches, a longitudinal length of 0.25 inches, and a distance from the longitudinal apex to the flat surface of the magnet of 0.044 inches. The focused magnets have a longitudinal magnetic origin. FIG. 14B depicts a comparison of attractive force between a pair of non-focused magnets and between different pairs of focused magnets similar to that depicted in FIG. 14A, but FIG. 14B depicts this comparison in terms of percentage increase in attractive force as a function of "air gap."

As can be seen in FIGS. 14A-14B, in some instances when the first and second focused magnets are in close proximity, both absolute and relative attractive force increase with decreasing magnetic radii of the first and second focused magnets. For example, when the air gap is about 0 mm (i.e., the magnets are touching or nearly touching), the attractive force between focused magnets having magnetic radii of about zero is about 157% greater than between the attractive force between non-focused magnets; the attractive force between focused magnets having magnetic radii of about 0.25 mm is about 104% greater than the attractive force between non-focused magnets; the attractive force between focused magnets having magnetic radii of about 0.5 mm is about 76% greater than the attractive force between nonmagnetic magnets; the attractive force between focused magnets having magnetic radii of about 0.75 mm is about 60% greater than that between non-focused magnets; the attractive force between focused magnets having magnetic radii of about 1 mm is about 50% greater than that between non-focused magnets; the attractive force between focused magnets having magnetic radii of about 2 mm is about 30% greater than that between non-focused magnets; and the attractive force between focused magnets having magnetic radii of about 4 mm is about 16% greater than that between non-focused magnets. Because the attractive force between focused magnets is a function of at least both magnetization radius and distance ("air gap") between the magnets, it may be desirable to have first and second magnets having magnetic radii that maximize the attractive force between the two magnets when they are a particular distance apart. More specifically, when the first and second magnets are respectively located in first and second catheters that may be used to create a fistula, the magnets may be located about 2 mm to about 4 mm apart, such as during catheter delivery toward a target fistula location. As the attractive force between the magnets pulls the catheters and magnets in closer approximation (as described in more detail below), the magnets may move to be less than about 0.5 mm apart. Therefore, in some variations, it may be desirable for the first and second magnets to have magnetic radii of approximately about 0.25 mm to about 0.5 mm or order to increase the attractive force through a range of air gaps from less than about 0.5 mm through about 2-4 mm. In other variations, it may be desirable for the first and second magnets to have magnetic radii of approximately about 0 mm to about 6 mm, about 0.1 mm to about 5 mm, about 0.2 mm to about 4 mm, about 0.3 mm to about 3 mm, about 0.4 mm to about 2 mm, about 0.5 mm to about 1 mm, or more than about 6 mm. It should be appreciated that while the exemplary attractive force shown in FIGS. 14A-14B is for multiple pairs of first and second magnets having magnetic radii identical to one another, in other variations, the first and second magnets may have magnetic radii different from one another.

Figure 15:
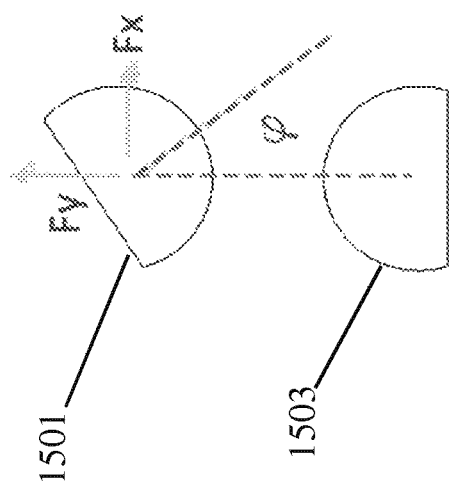
FIG. 15 is an illustrative depiction of a transverse cross-section of a rotationally misaligned magnet pair.
Figure 16:
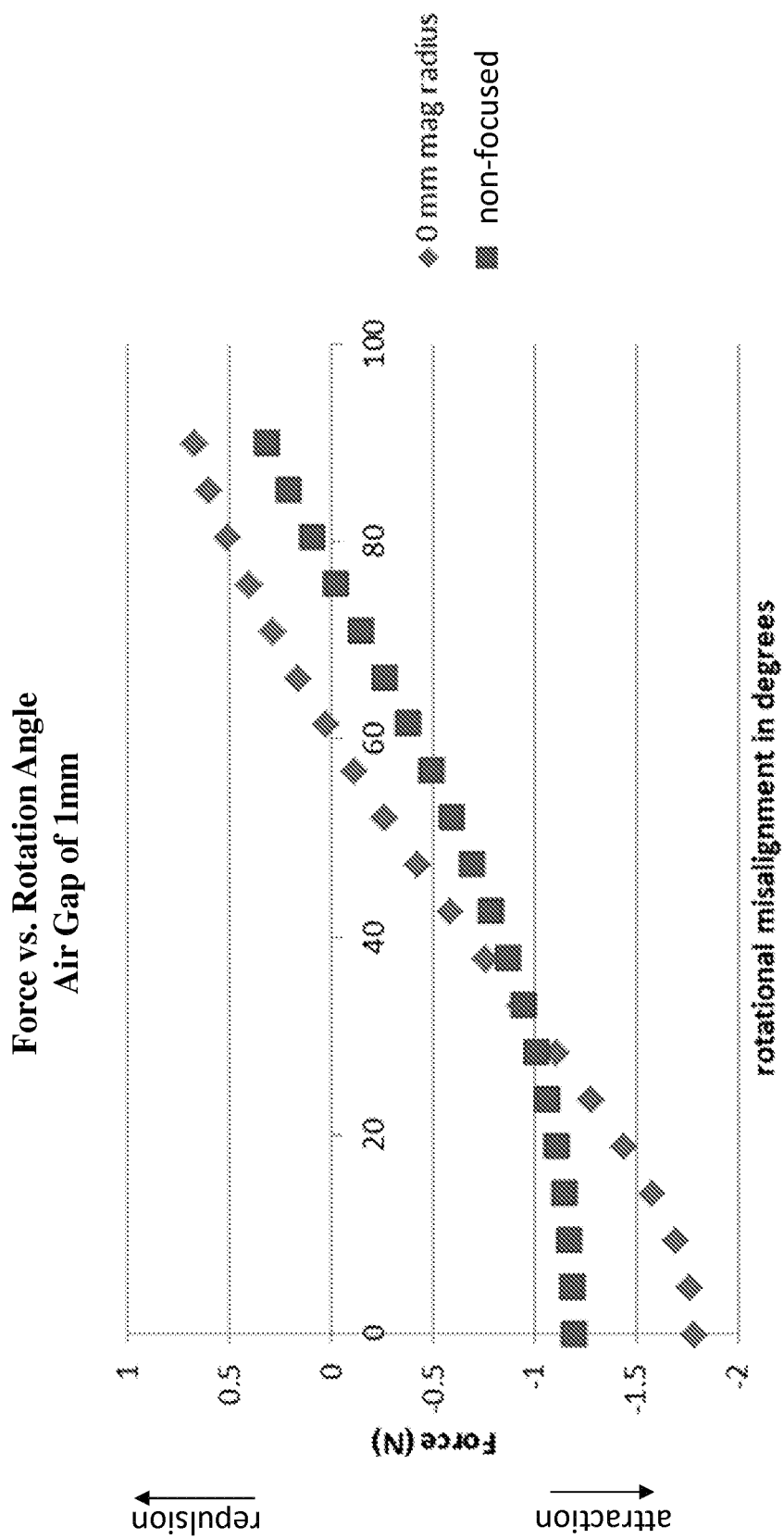
FIG. 16 depicts the attractive force between first and second magnets as a function of the rotation angle of the first magnet relative to the second magnet.

As mentioned briefly above, the amount of attractive force between two magnets may depend at least partially on the relative rotational alignment of the first and second magnets. For example, as shown in FIG. 15, a first magnet (1501) and a second magnet (1503) may be approximate each other and rotated relative to one another by an angle φ (referred to hereinafter as the "rotational misalignment"). First and second magnets (1501) and (1503) may be non-focused magnets or focused magnets. The attractive force between the first and second magnets (1501) and (1503) is depicted as Fy. FIG. 16 depicts a comparison of the attractive force between a pair of non-focused magnets and the attractive force between a pair of focused magnets having magnetization radii of about 0 mm, as a function of rotational misalignment. The magnets within each magnet pair of FIG. 16 are separated by a distance of about 1 mm, and are N52 NdFeB magnets each having a D-shaped transverse cross-section, a diameter of 0.0675 inches, a longitudinal length of 0.25 inches, and a distance from the apex to the flat surface of the magnet of 0.044 inches. As shown in FIG. 16, the attractive force is greatest when the first and second magnets are rotationally aligned (i.e., when the rotational misalignment is zero). The attractive force decreases as the rotational misalignment increases. At low rotational misalignments (e.g., in the example here below about 35 degrees), the attractive force is greater between focused magnets than between non-focused magnets.

In contrast, however, at high rotational misalignments (e.g., in the example here, above about 35 degrees), the attractive force between focused magnets is less than that between non-focused magnets. One practical effect of this relationship is that two focused magnets, separated by a given distance, have a lower tendency to attract one another at high rotational misalignment, compared to two non-focused magnets separated by the same distance and similarly rotationally misaligned. Low attractive force between significantly rotationally misaligned magnets may be desirable to prevent the magnets from moving toward each other when significantly misaligned. When the magnets are located within catheters as described herein, this may prevent the first and second catheters from moving into closer approximation when a fistula-forming element of a first catheter (such as fistula-forming element (109) described above) is not properly aligned with a recess of a second catheter configured to receive the fistula-forming element (such as recess (117) described above).

Thus, focused magnets may have higher attractive force at low rotational misalignment and lower attractive force at high rotational misalignment, as compared to non-focused magnets. Put another way, the rate of decrease in attractive force as a function of rotational misalignment (i.e., the slope of the curves in FIG. 16) may increase with decreasing magnetic radii of the first and second magnets. For example, in the example of FIG. 16, the attractive force between non-focused magnets decreases by about 50% when rotational misalignment is about 50 degrees, relative to its maximum at 0 degrees of rotational misalignment. In contrast, the attractive force between focused magnets with 0 mm magnetization radii decreases by about 50% when rotational misalignment reaches about 35 degrees, relative to its maximum at 0 degrees of rotational misalignment.

Magnets—Restoring Torque

Figure 17A:
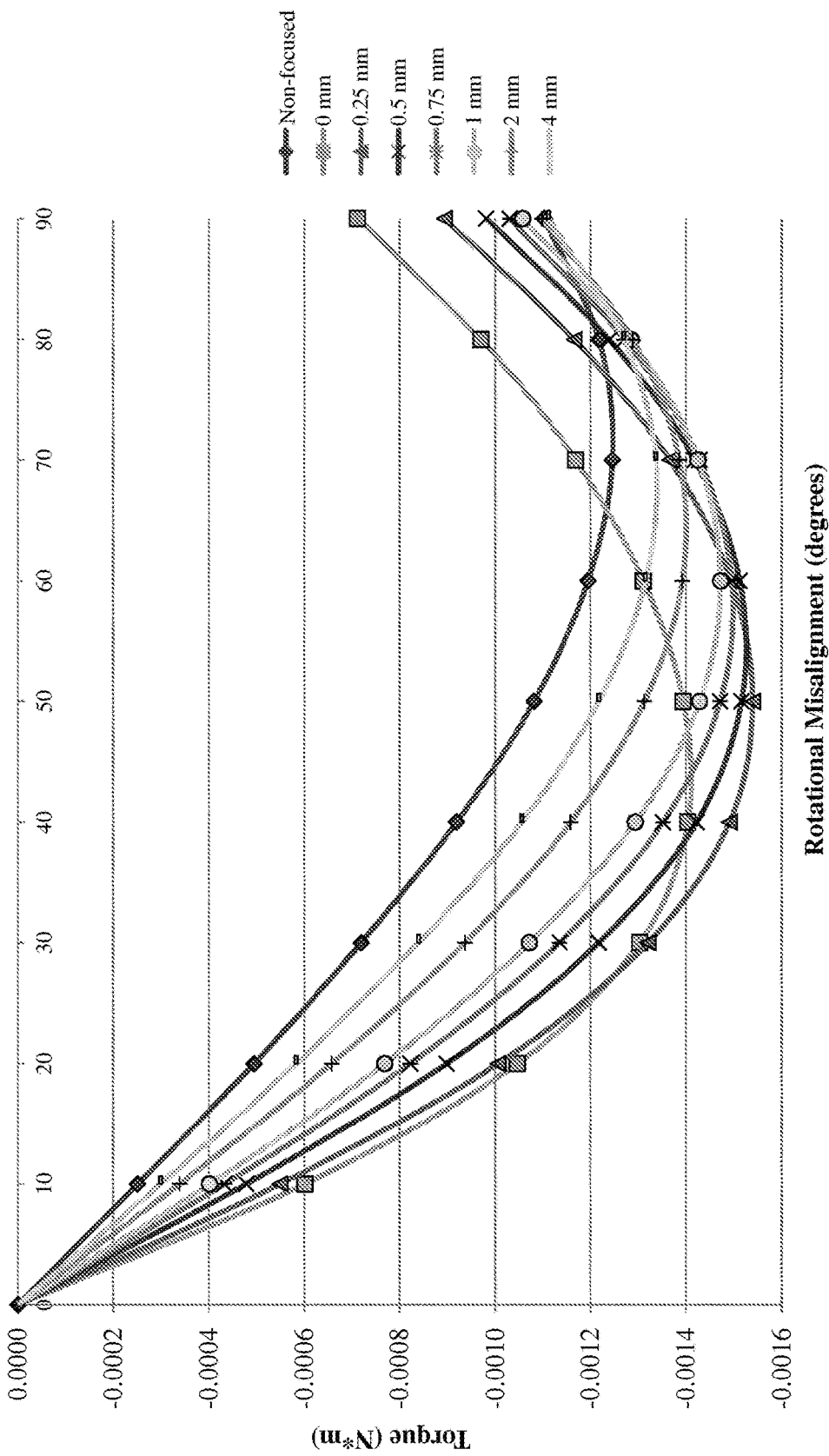
FIGS. 17A and 18 depict the restoring torque between two magnets suitable for use with the catheters described here as a function of the rotational misalignment between the two magnets.
Figure 17B:
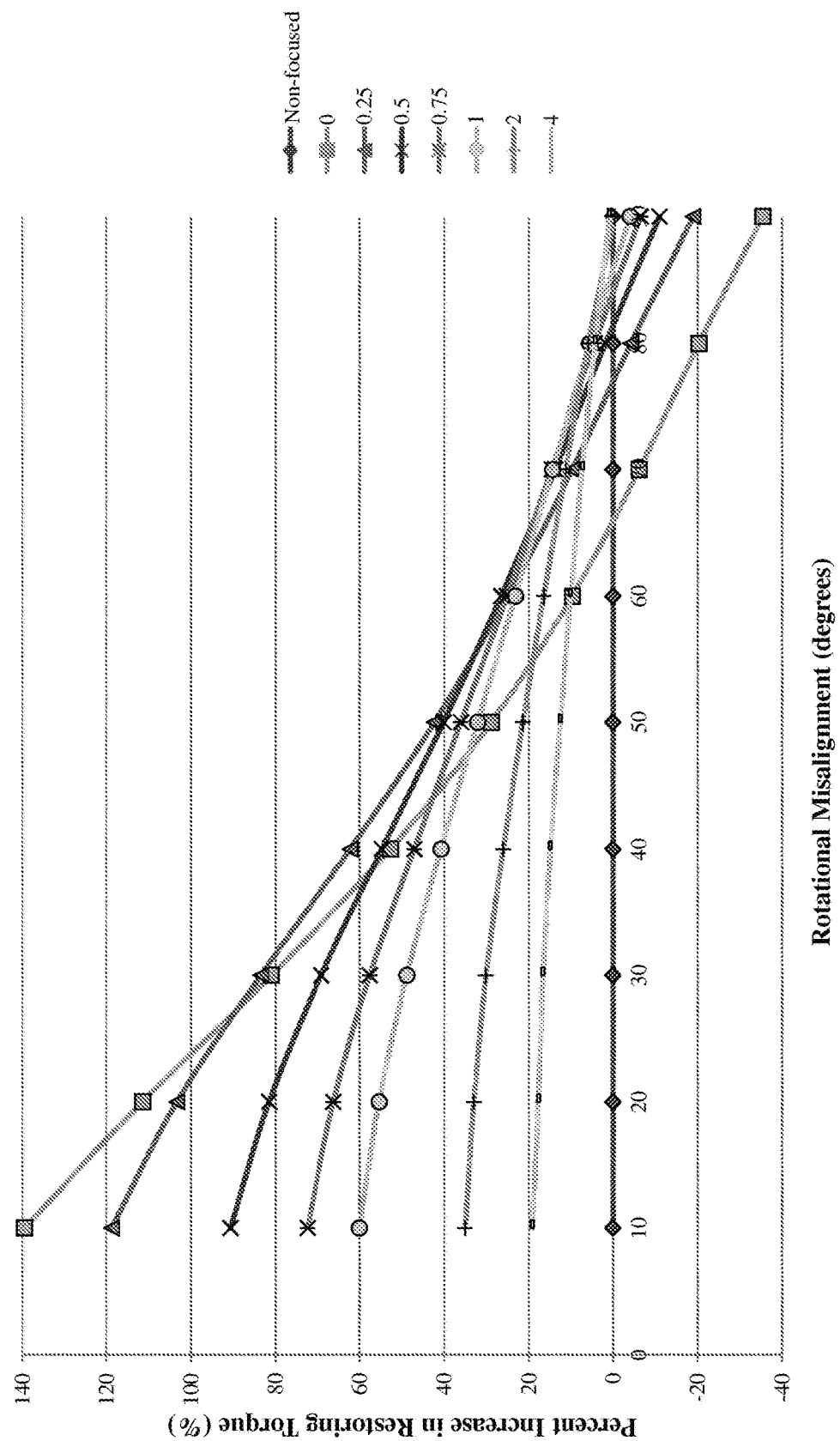
FIG. 17B depicts the percentage increase in the restoring torque between the magnets of FIG. 17A as a function of the rotational misalignment between the two magnets.
Figure 18:
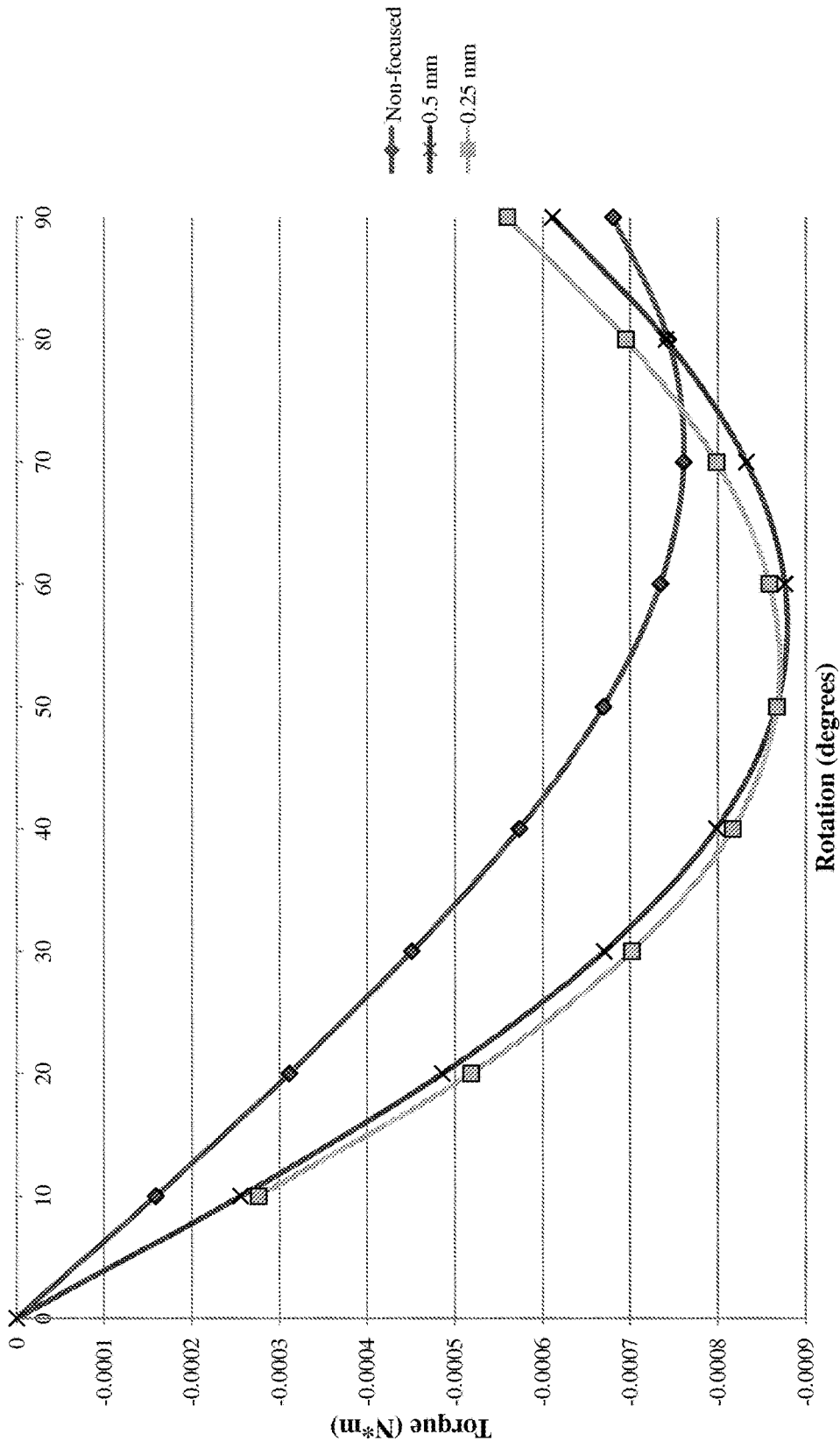

Different magnet pairs may have different torque urging the magnets to rotationally align (i.e., "restoring torque"). FIGS. 17A-17B and FIG. 18 depict a comparison of the amount of restoring torque between a pair of first and second magnets, for different kinds of magnet pairs. In particular, FIG. 17A depicts the restoring torque between first and second magnets located about 0.5 mm apart as a function of rotational misalignment, for non-focused magnets and focused magnets having longitudinal magnetic origins with a range of magnetic radii. The non-focused and focused magnets comprise N52 NdFeB magnets each having a D-shaped transverse cross-section, a diameter of 0.0675 inches, a longitudinal length of 0.25 inches, and a distance from the apex to the flat surface of the magnet of 0.044 inches. FIG. 17B depicts a comparison of restoring torque between a pair of non-focused magnets and between different pairs of focused magnets similar to that depicted in FIG. 17A, but FIG. 17B depicts this comparison in terms of percentage increase in attractive force as a function of rotational misalignment. FIG. 18 depicts the restoring torque between the first and second magnets as a function of rotational misalignment for non-focused magnets and focused magnets having a range of magnetic radii, when the first and second magnets are located about 1 mm apart.

As shown in FIGS. 17A-17B and FIG. 18, at small rotational misalignments (e.g., less than about 30 degrees), restoring torque increases with decreasing magnetic radii of the first and second magnets. For example, as shown in FIG. 17B, when the air gap is about 0.5 mm and the rotational misalignment is about 10%, the restoring torque between focused magnets having magnetic radii of about zero is about 140% greater than that between non-focused magnets; the restoring torque between focused magnets having magnetic radii of about 0.25 mm is about 119% greater than that between non-focused magnets; the restoring torque between focused magnets having magnetic radii of about 0.5 mm is about 91% greater than that between non-focused magnets; the restoring torque between focused magnets having magnetic radii of about 0.75 mm is about 72% greater than that between non-focused magnets; the restoring torque between focused magnets having magnetic radii of about 1 mm is about 60% greater than that between non-focused magnets; the restoring torque between focused magnets having magnetic radii of about 2 mm is about 35% greater than that between non-focused magnets; and the restoring torque between focused magnets having magnetic radii of about 4 mm is about 19% greater than that between non-focused magnets.

Figure 19A:
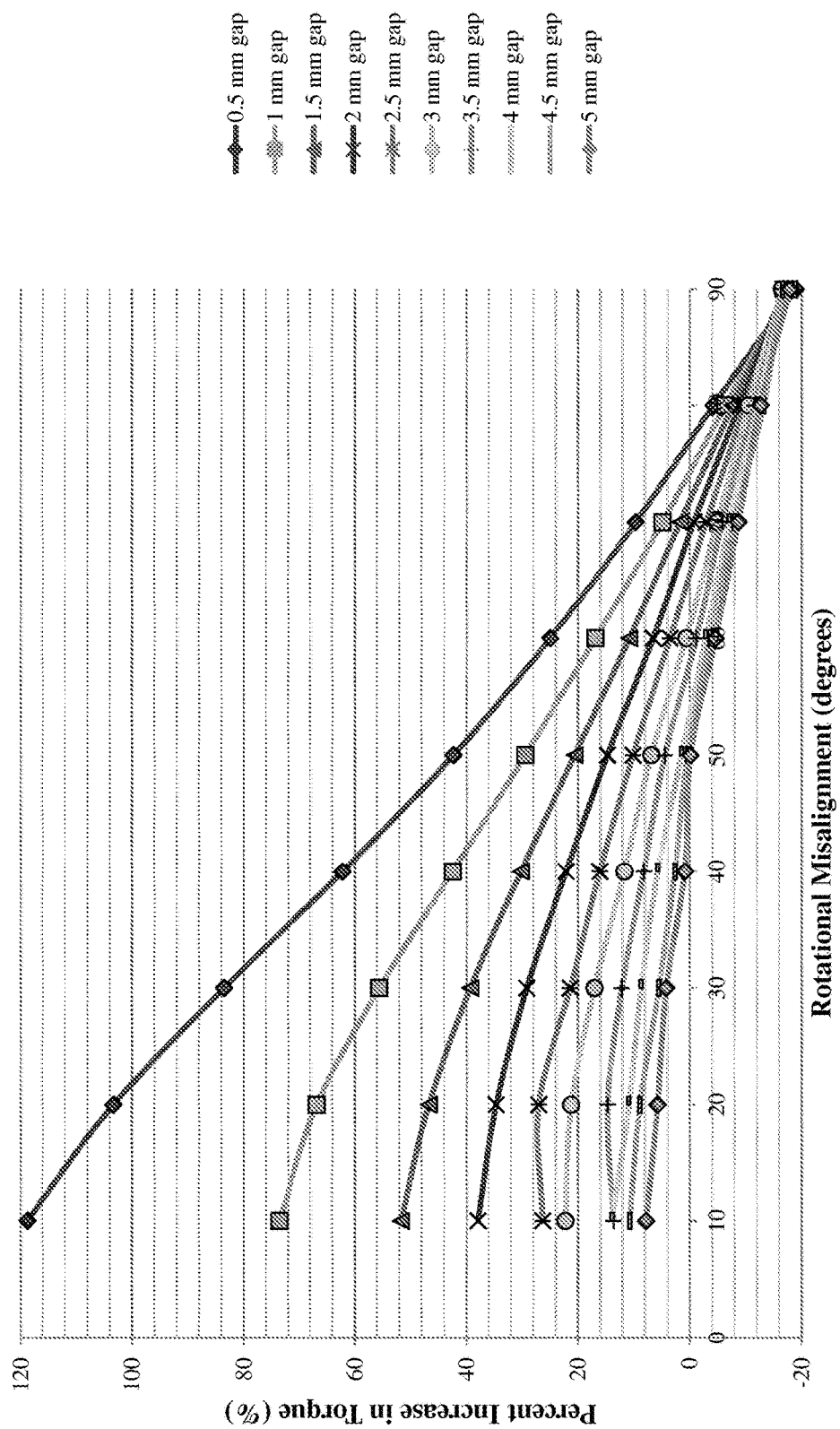
FIGS. 19A and 19B depict the percentage increase in restoring torque between two magnets suitable for use with the catheters described here as a function of the rotational misalignment between the two magnets.
Figure 19B:
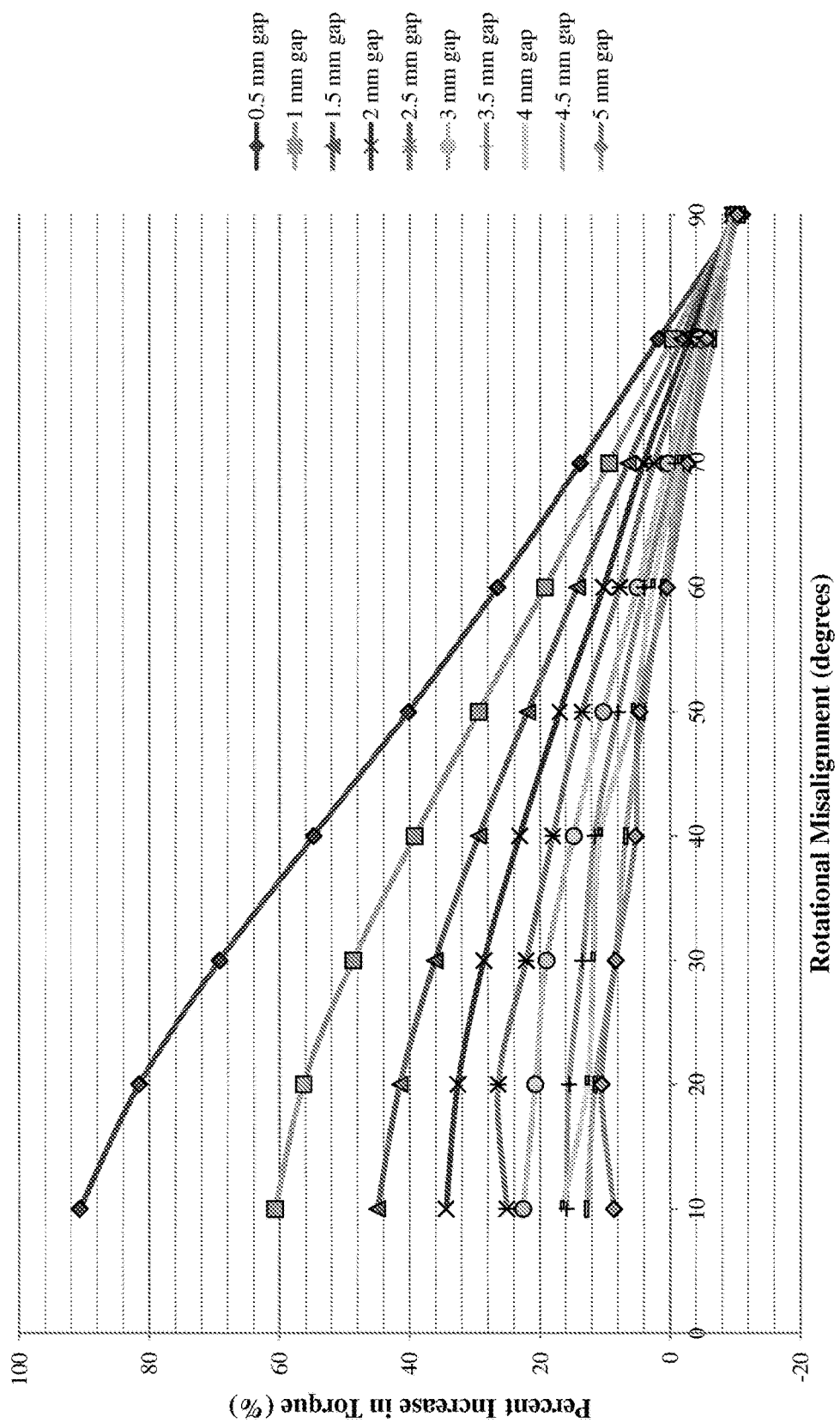

FIGS. 19A and 19B depict the percentage increase, relative to non-focused magnets of similar dimension, in restoring torque between a pair of focused magnets as a function of the rotational misalignment between the two magnets, for a range of "air gap" distances between the first and second magnets. FIG. 19A depicts such a percentage increase in restoring torque in magnets having magnetic radii of about 0.25 mm, while FIG. 19B depicts such a percentage increase in restoring torque in magnets having magnetic radii of about 0.5 mm. As shown in FIGS. 19A and 19B, for any given rotational misalignment between two focused magnets, the percentage increase in restoring torque generally increases with decreasing "air gap" distance between the two magnets. That is, the restoring torque is greater when the two magnets are closer together.

In some variations, the first and second catheters may respectively comprise focused magnets, and the focused magnets may be configured such that restoring torque is greater than the restoring torque between two non-focused magnets of similar dimensions and materials. This may allow the catheters to overcome greater rotational stiffness to help bring the catheters into rotational alignment, and may allow the restoring torque between the catheters to be increased when the size of the catheters (and the magnets thereof) is otherwise constrained. It may be desirable to ensure proper rotational alignment of the catheters in order to promote proper formation of the fistula using the one or more fistula forming elements, as described above. The amount of increased restoring torque between a pair of first and second focused magnets may depend on the rotational alignment of the first and second magnets, the magnetic radii of the first and second magnets, and/or on the distance between the first and second magnets.

Magnets—Permeance Coefficient

Focused magnets may, in some instances, have a different permeance coefficient than non-focused magnets. As a result, focused magnets may experience less demagnetization under various demagnetization stresses (e.g., opposing magnetic fields, elevated temperature), thereby resulting in increased magnetic flux density, or magnetic force. This may be particularly desirable in magnets having low intrinsic coercivity, such as neodymium magnets (e.g., N52 magnets).

Figure 20B:
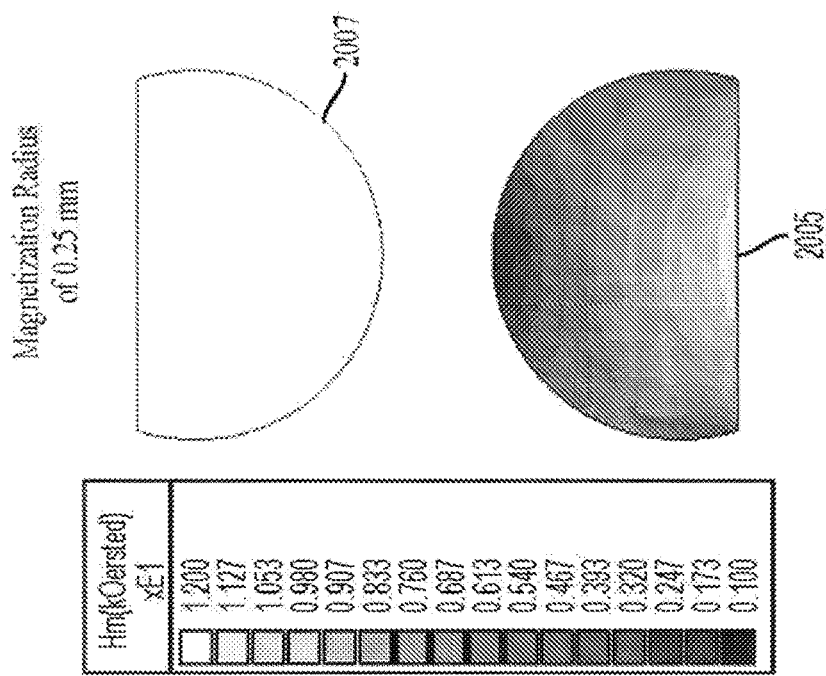
FIGS. 20A and 20B depict transverse cross-sections of demagnetization profiles of magnets having approximately D-shaped cross sections and having parallel magnetic flux vectors and non-parallel magnetic flux vectors, respectively.
Figure 20A:
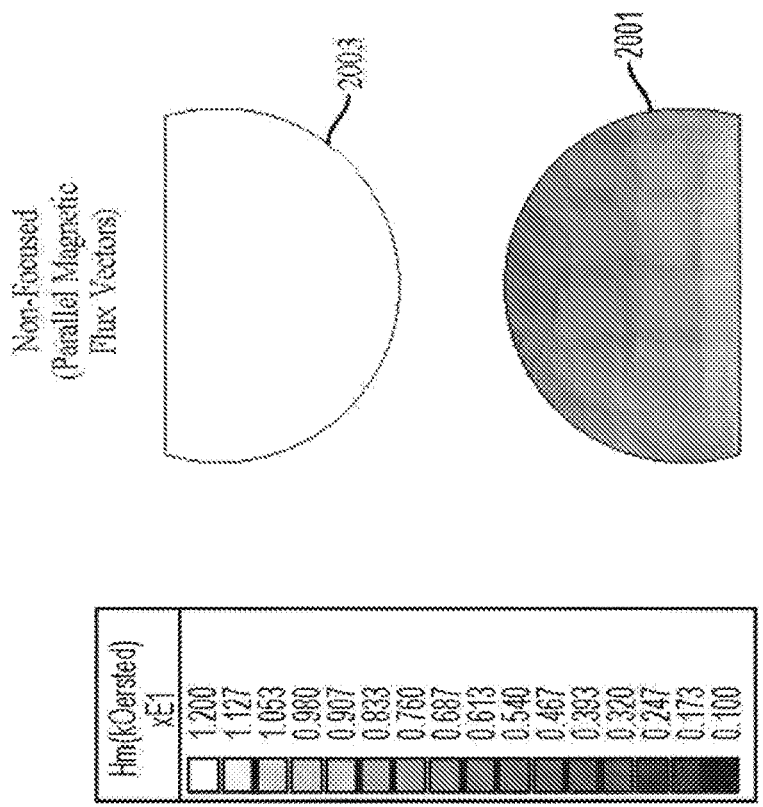

Furthermore, focused magnets may also experience less demagnetization in magnetic domains that contribute most to generation of an attractive force. For example, FIG. 20A depicts the transverse cross-sections of two opposing non-focused D-shaped N52 magnets (2001) and (2003) having parallel magnetic flux vectors. FIG. 20B depicts the transverse cross-sections of two opposing focused D-shaped N52 NdFeB magnets (2005) and (2007) having magnetization radii of about 0.25 mm and longitudinal magnetic origins, where the magnets are separated by an air gap of about 0.5 mm. In the depicted arrangement, the region of a one magnet that is closest to the opposing magnet may make the greatest contribution to the magnetic flux density, or magnetic force, to the air gap between the opposing magnets. For example, the convex region of magnet (2001) makes the greatest contribution to magnetic flux density in the air gap between magnets (2001) and (2003), while the convex region of magnet (2005) makes the greatest contribution to magnetic flux density in the air gap between magnets (2005) and (2007).

FIGS. 20A and 20B also depict demagnetization profiles of the non-focused magnet (2001) and focused magnet (2005), respectively. As can be seen by comparing the demagnetization profiles of magnets (2001) and (2005), the non-focused magnet (2001) experiences a more uniform demagnetization than the focused magnet (2005). In contrast, focused magnet (2005) experiences less demagnetization in its convex region located closest to the opposing magnet (2007). The decreased demagnetization in the convex region of focused magnet (2005) may increase the magnetic flux density, or magnetic force, in the region between the magnets (2005) and (2007). Thus, in some variations as a result of decreased demagnetization in crucial magnet regions, the use of focused magnets in such an arrangement (such as in catheters described herein) may provide increased attractive force and restoring torque between the magnets.

Other Magnet Configurations

It should be appreciated that the above-described trends regarding attractive force, restoring torque, and demagnetization may also be similarly developed in focused magnets having transverse magnetic origins, and may also be similarly developed in focused magnets having magnetic origins comprising a single point, and/or any suitable kind of magnetic origin. Moreover, the above-described trends regarding attractive force, restoring torque, and demagnetization may also be similarly developed in focused magnets having other magnet shapes and dimensions. It should further be appreciated that the above-described trends may also be similarly developed in a focused magnet pair in which the first and second focused magnets do not have the same materials or dimensions.

Figure 21:
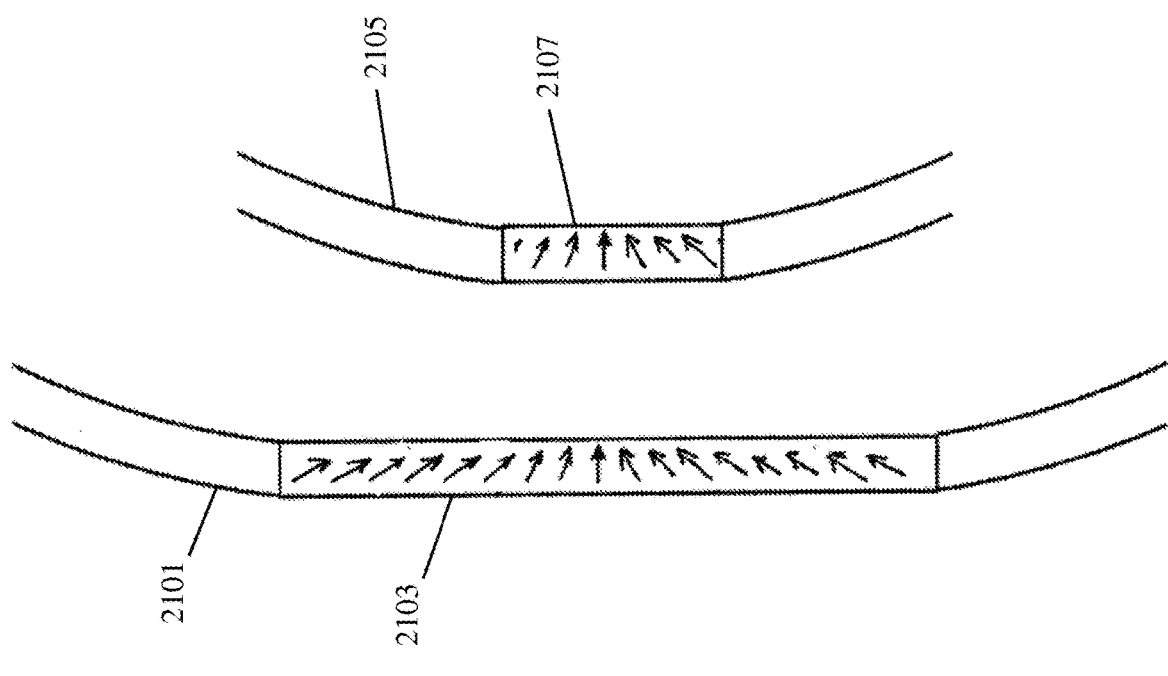
FIG. 21 is an illustrative depiction of a cross-section of a variation of a catheter pair comprising magnets described here.

For example, as shown in FIG. 21, in some instances in which a first catheter (2101) comprises a first magnet (2103) and a second catheter (2105) comprises a second magnet (2107), the first magnet (2103) may be longer than the second magnet (2107). When the first catheter is in a first blood vessel, and the second catheter is in a second blood vessel, the shorter second magnet may aid in bringing the first and second blood vessels together in apposition. In particular, the attractive force of the longer first magnet may act upon a smaller area of the second magnet due to the shorter length of the second magnet, which in turn may increase the pressure that is generated by the second magnet on the wall of the second blood vessel. This increased pressure may facilitate better apposition of the first and second blood vessels, such as for better and/or easier fistula formation. A shorter second magnet may be desirable in a number of situations, such as when two vessels between which a fistula is intended to be formed overlap over only a short distance. Additionally, a shorter second magnet may be placed in an area of a vessel having greater curvature. As another example, when a stiffer substance (e.g., muscle, fat, fascia, cartilage, bone) exists between the vessels immediately upstream or downstream of a target fistula formation site and hampers vessel apposition around the target fistula formation site, use of a shorter second magnet may allow a smaller available segment of the second vessel to be deflected toward the first vessel for fistula formation.

Although the focused magnets discussed above may be characterized by magnetization patterns comprising magnetic flux vectors each passing through a single magnetic origin (e.g., a point or line), in other variations, a similar effect with respect to attractive force, restoring torque, and demagnetization may be achieved with magnets comprising a combination of two or more regions, where each region is individually "non-focused"—that is, the magnetic domains within each region have substantially parallel magnetic flux vectors. In particular, in some variations, a focused magnet may include multiple regions, where the magnetization pattern of each region is represented by a plurality of magnetic flux vectors substantially oriented in parallel to each other within each region, while the magnetic flux vectors of a first region are oriented in a different direction than those in a second region. When combined in a particular manner, the "non-focused" regions of a magnet collectively provide a similar effect as a "focused" magnet described above.

In some variations, two or more non-focused regions may be combined to form a magnet with an effective longitudinal magnetic origin (i.e., to collectively approximate a focused magnet). For example, FIGS. 22B and 22C illustrate D-shaped transverse cross-sections of magnets (2201) and (2203), respectively, which are similar in shape to the longitudinal magnet (2204) depicted in FIG. 22A. In one variation, as shown in FIG. 22B, magnet (2201) may comprise a first region (2205) with a first non-focused magnetization pattern represented by a first set of parallel magnetic flux vectors (2209), and a second region (2207) with a second non-focused magnetization pattern represented by a second set of parallel magnetic flux vectors (2211). As described from the perspective of FIG. 22B, the first domain (2205) may be located to the left of the midline of the transverse cross-section, and the second domain (2207) may be located to the right of the midline of the transverse cross-section. The first and second sets of magnetic flux vectors (2209) and (2211) may be oriented toward the midline of the transverse cross-section by angles $\alpha 1$ and $\alpha 2$, respectively, of approximately 45 degrees. The components of the magnetic flux vectors (2209) and (2211) pointed upwards may at least partially augment each other, while the components of the magnetic flux vectors (2209) and (2211) pointed to the right and left as may at least partially cancel each other. Accordingly, the summed effective magnetic flux density is focused near the apex of the magnet (2201) to form an effective longitudinal magnetic origin, similar to the focused magnets described with reference to FIGS. 2A-11B.

In another variation, as shown in FIG. 22C, a magnet (1303) may comprise four domains: a first region (2213), a second region (2215), a third region (2217), and a fourth region (2219), in order from left to right as depicted in FIG. 22C. The first, second, third, and fourth regions have respective non-focused magnetization patterns represented by respective sets of parallel magnetic flux vectors (2221), (2223), (2225), and (2227). The first and fourth sets of magnetic flux vectors (2221) and (2227) are oriented toward the midline of the transverse cross-section by angles $\alpha 1$ and $\alpha 2$, respectively, of approximately 45 degrees. The second and third sets of magnetic flux vectors (2223) and (2225) may be directed upward toward the apex of the cross-section. The components of the magnetic flux vectors (2221) and (2227) that are pointed upwards may at least partially augment each other and may further combine with the upward magnetic flux vectors (2223) and (2225), while the components of the magnetic flux vectors (2221) and (2227) pointed to the right and left may at least partially cancel each other. Accordingly, the summed effective magnetic flux density is focused near the apex of the magnet (2203) to form an effective longitudinal magnetic origin, similar to the focused magnets described with reference to FIGS. 2A-11B.

It should be appreciated that in other variations, the magnetic flux vectors (2209) and (2211) (in FIG. 22B) and magnetic flux vectors (2221) and (2227) (in FIG. 22C) may be oriented at any suitable angles $\alpha 1$ and $\alpha 2$ to produce an effective magnetic origin at any suitable location (e.g., a longitudinal magnetic origin with any suitable magnetization radius). For instance, decreasing angles $\alpha 1$ and $\alpha 2$ may increase the effective magnetization radius, while increasing angles $\alpha 1$ and $\alpha 2$ may decrease the effective magnetization radius. Furthermore, angles $\alpha 1$ and $\alpha 2$ may be approximately equal to generate an effective magnetic origin substantially aligned with the midline of the transverse cross-section, or angles $\alpha 1$ and $\alpha 2$ may be unequal to generate an effective magnetic origin in other locations.

In other variations, two or more non-focused regions may be combined to form a magnet with an effective transverse magnetic origin. For example, FIG. 23A depicts a magnet (2304) with a longitudinal axis and a D-shaped transverse cross-section. FIG. 23B depicts a longitudinal cross-section of the magnet (2304). Magnet (2304) may comprise a first region (2331), a second region (2333), and a third region (2335). The first, second, and third regions have non-focused magnetization patterns represented by first, second, and third sets of parallel magnetic flux vectors (2337), (2339), and (2341), respectively. The first and third sets of magnetic flux vectors (2337) and (2341) may be oriented toward the midline of the longitudinal cross-section by angles $\alpha 1$ and $\alpha 2$, respectively, of approximately 45 degrees. The components of the magnetic flux vectors (2337) and (2341) that are pointed upwards as depicted in FIG. 23B may at least partially augment each other and may combine with the upward magnetic flux vectors (2339), while the components of the magnetic flux vectors (2337) pointing right and the components of the magnetic flux vectors (2341) pointing left, as depicted in FIG. 23B, may at least partially cancel each other. Accordingly, the summed effective magnetic flux density is focused so as to form an effective transverse magnetic origin, similar to the focused magnets described with reference to FIGS. 12A and 12B. It should be appreciated that in other variations, the magnetic flux vectors (2337) and (2341) may be oriented at any suitable angles $\alpha 1$ and $\alpha 2$ to produce an effective magnetic origin at any suitable location (e.g., a transverse magnetic origin with any suitable magnetization radius). For instance, decreasing angles $\alpha 1$ and $\alpha 2$ may increase the effective magnetization radius, while increasing angles $\alpha 1$ and $\alpha 2$ may decrease the effective magnetization radius. Furthermore, angles $\alpha 1$ and $\alpha 2$ may be approximately equal to generate an effective magnetic origin substantially aligned with the midline of the longitudinal cross-section, or angles $\alpha 1$ and $\alpha 2$ may be unequal to generate an effective magnetic origin in other locations.

In yet other variations, the principles described with reference to FIGS. 22A-22C and FIGS. 23A-23B may be combined in any suitable manner, such that a magnet with two or more domains has an effective magnetic origin in the form of a single point, or any suitable line. For example, multiple "non-focused" regions may be combined in such a manner that the resulting magnet may have an effective magnetic origin that is somewhere between a longitudinal magnetic origin and a transverse magnetic origin.

In some variations, the multiple non-focused regions may be formed in a single magnet by applying a desired magnetic field to different regions of pressed powder, as described in further detail below. In other variations, the multiple non-focused regions may be embodied in separately-formed magnets that are subsequently bonded or otherwise combined together, such as through epoxy or fit together within an external case or shrink wrap. For example, with reference to FIG. 22B, a first region (2205) may be embodied in a first non-focused magnet having a half D-shaped cross-section, and a second region (2207) may be embodied in a second non-focused magnet having a half D-shaped cross-section. The first and second non-focused magnets may be combined to form a larger magnet with an approximately D-shaped transverse cross-section as shown in FIG. 22B, such as through epoxy or by fitting both non-focused magnets into a casing having a semi-circular cross-section. Other suitable shapes of separate non-focused magnets, such as those depicted in FIG. 22C or 23A-23B or other suitable magnet shapes and sizes, may similarly be combined to form a larger magnet.

Figure 24:
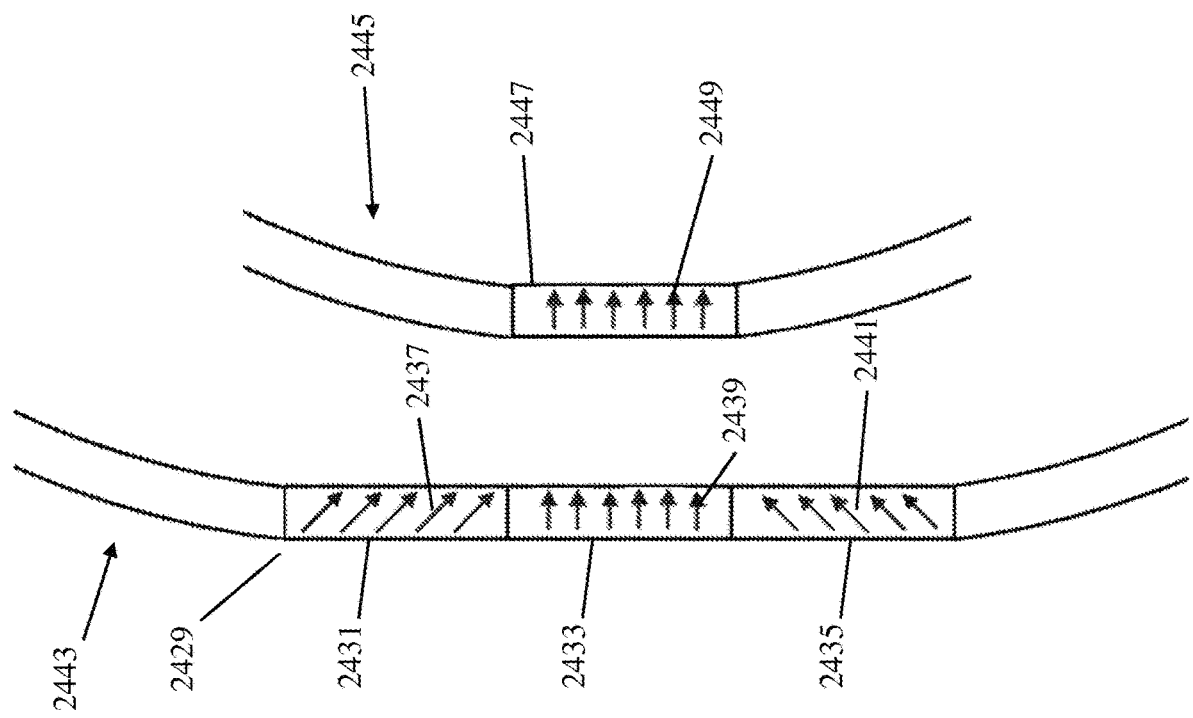
FIG. 24 is an illustrative depiction of a cross-section of a variation of a catheter pair comprising magnets described here.

In some variations, such as shown in FIG. 24, a first catheter (2443) such as described above may comprise a magnet similar to that depicted in FIG. 23B, while a second catheter (2445) as described above may comprise a shorter magnet (2447) having parallel magnetic flux vectors (2449) oriented in the same direction as magnetic flux vectors (2439) in a region of first catheter (2443). This arrangement may have similar effects as described above with respect to the catheter and magnet pairs of FIG. 21. It should be appreciated that while FIGS. 22A-24 depict magnets comprising two, four, and three non-focused regions, respectively, in other variations magnets as described herein may comprise any suitable number of regions (e.g., two, three, four, five, six, or more regions).

It should be appreciated that although in some variations the magnets discussed above have been described as pairs, a catheter system may utilize any combination of magnets as described here. For example, when the systems described here comprise a first catheter and a second catheter, either the first and/or second catheter may have more than one magnet, which may comprise any combination of the magnets described here, as described in more detail above.

Systems

Also described here are systems for forming a fistula between two blood vessels. Generally, the systems may comprise a first catheter, which may comprise one or more fistula-forming elements and one or more magnets. The first catheter may comprise any one or more of any of the fistula-forming elements or combination of fistula-forming elements as described in more detail above and in U.S. patent application Ser. No. 13/298,169, which was previously incorporated by reference in its entirety. The first catheter may comprise one or more magnets, which may be any of the magnets described in more detail above. The first catheter may comprise any suitable catheter body and may comprise one or more other elements, such as one or more shape-changing elements or balloons such as described in more detail in U.S. patent application Ser. No. 13/298,169, which was previously incorporated by reference in its entirety.

The systems described here may also comprise a second catheter. In some variations, the second catheter may comprise a fistula-forming element and one or more magnets, but need not. In variations where the second catheter does comprise a fistula-forming element, the second catheter may comprise any one or more of any of the fistula-forming elements or combination of fistula-forming elements as described in more detail above and in U.S. patent application Ser. No. 13/298,169, which was previously incorporated by reference in its entirety. The fistula-forming element of the second catheter may be the same as or different from the fistula-forming element of the first catheter. The second catheter may comprise one or more magnets, which may be any of the magnets described in more detail above. The second catheter may comprise any suitable catheter body and may comprise one or more other elements, such as one or more shape-changing elements or balloons such as described in more detail in U.S. patent application Ser. No. 13/298,169, which was previously incorporated by reference in its entirety.

Methods

Methods of Manufacture

Also described here are methods for manufacturing magnets with specialized magnetization patterns, each magnetization pattern comprising a plurality of magnetic domains, where each magnetic domain is represented by a magnetic flux vector that passes through a common magnetic origin (e.g., a point or line). In some instances, the magnets described here may be manufactured by compressing a powder in a die while applying a magnetic field to the powder. The applied magnetic field may match the desired orientation of the magnetic flux vector at each magnetic domain and cause each particle of the powder to elongate either parallel or perpendicular to the orientation of the applied magnetic field. The desired applied magnetic field shape may be created by placing the powder within a magnetically permeable fixture, which directs the field in the desired shape through the powder.

Figure 25A:
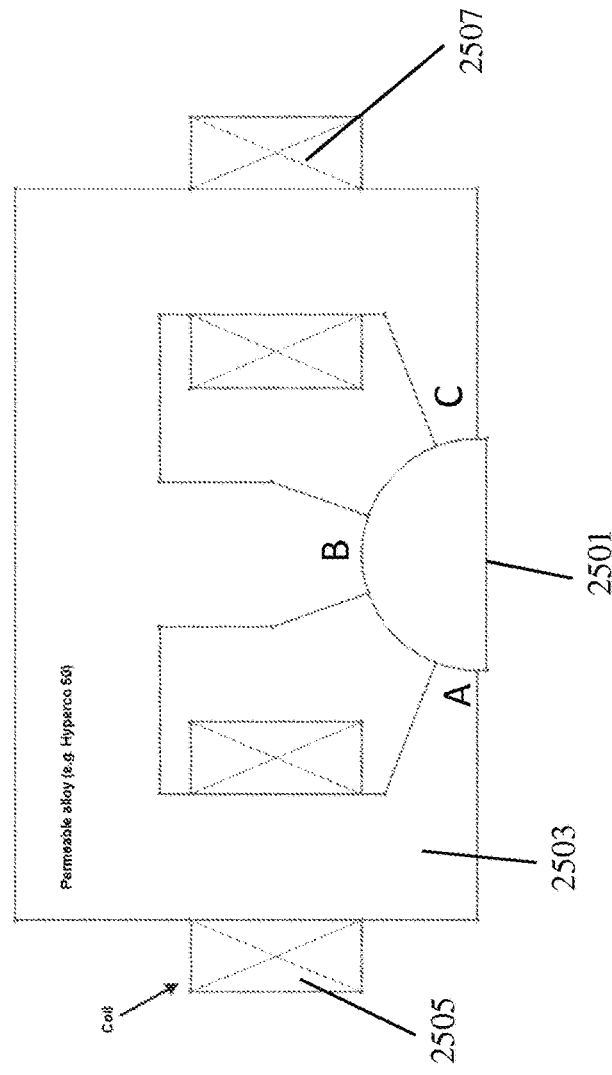
FIG. 25A depicts a cross-section of a magnet, fixture, and coils used to manufacture variations of magnets described here.
Figure 25B:
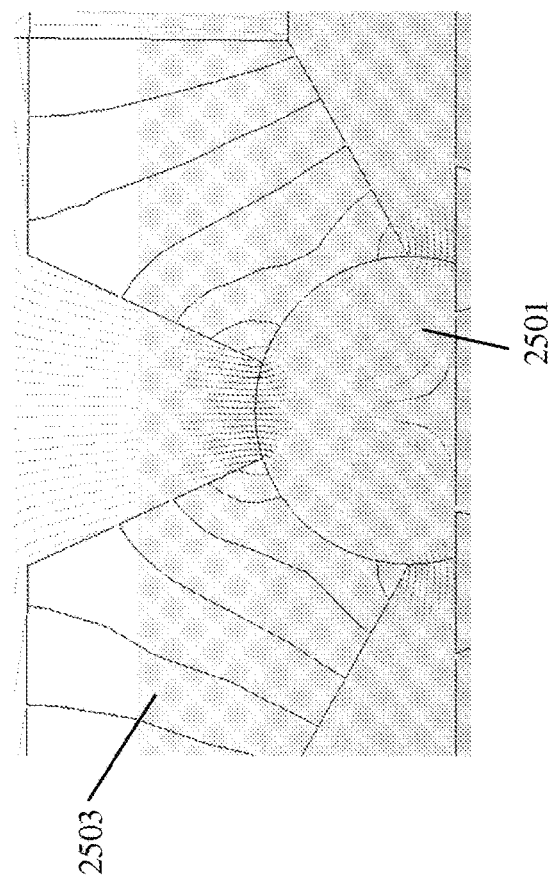
FIG. 25B depicts a portion of the cross-section of FIG. 25A showing the magnetic flux generated by the coils.

The fixture may comprise a highly permeable alloy, such as Hyperco 50. In other variations, the magnets may comprise isotropic magnets (e.g., bonded neodymium or bonded samarium-cobalt magnets), which may be magnetized in any orientation without being premagnetized in the direction of the desired magnetic flux vectors as described above. FIG. 25A depicts a transverse cross-section of a magnet (2501), a fixture (2503), and two coils (2505) and (2507) that may be used to generate the magnetic flux. As shown, the fixture (2503) may contact the magnet (2501) at three points (A), (B), and (C) around the magnet's outer surface. FIG. 25B depicts the resulting magnetic flux directed through the magnet (2501).

The resulting magnetization radius (i.e., the location of the magnetic origin) of the magnet is determined by the relationship between the fixture contact points and the magnet. In particular, changing the location of the three points around the magnet's outer surface may change the resulting magnetization radius of the magnet. For example, moving the left and right contact points downward as depicted in FIGS. 25A-25B (i.e., to wrap around the corners of the magnet (2501) to contact the flat face of the magnet) may change the magnetization radius of the magnet (2501).

Methods of Creating a Fistula

Also described here are methods for creating a fistula between two blood vessels. The two blood vessels may be two closely-associated blood vessels, such as a vein and an artery, two veins, etc. Generally, in these methods, catheters comprising magnets as described above may be used to bring the two vessels toward each other. After the vessels are brought toward each other, one or more fistula-forming elements may be activated to bore through, perforate, or otherwise create a passageway between the two blood vessels such that blood may flow directly between the two adjoining blood vessels. When such a fistula is formed, hemostasis may be created without the need for a separate device or structure (e.g., a suture, stent, shunt, or the like) connecting or joining the blood vessels.

Generally, the methods described here comprise accessing a first blood vessel with a first catheter, and advancing the first catheter to a target location within a blood vessel. A second blood vessel may be accessed with a second catheter, and the second catheter may be advanced to a target location within the second vessel. In some of these methods, both the first and second catheters may comprise magnets each characterized by a magnetization pattern comprising magnetic flux vectors passing through a common magnetic origin, as described in more detail above. The first catheter may be advanced into an artery, and the second catheter may be advanced into a vein. In other methods, the first catheter may be advanced into a first vein and the second catheter may be advanced into a second vein. In yet other methods, the first catheter may be advanced into a first artery and the second catheter may be advanced into a second artery. The catheters may be advanced in any suitable manner, as described in more detail in U.S. patent application Ser. No. 13/298,169, which was previously incorporated by reference in its entirety, and any of the catheters described in that application may be used.

Once the first and/or second catheters have been advanced into the respective blood vessels, the catheters may be adjusted to affect the positioning of the catheters within the blood vessels and/or the positioning of the blood vessels relative to each other. The magnets of the first and second catheters may result in an attractive force between the catheters, which may pull the catheters toward each other. The magnets may also result in a torque causing the two catheters to rotationally align. For example, the first and/or second catheters may comprise one or more magnets having a magnetization pattern such as described in more detail above.

Once the catheter or catheters have been positioned and adjusted, one or more fistula-forming elements may be used to create a fistula between the two blood vessels. Any of the methods for using fistula-forming elements to create one or more fistulas described in U.S. patent application Ser. No. 13/298,169, which was previously incorporated by reference in its entirety, may be used.

We claim:

1. A method of forming a fistula between a first blood vessel and a second blood vessel of a patient, comprising:
    advancing a first catheter into the first blood vessel, wherein the first catheter comprises a first magnet;
    advancing a second catheter into the second blood vessel, wherein the second catheter comprises a second magnet, and wherein at least one of the first and second catheters comprises a fistula-forming element;
    moving the first catheter toward the second catheter using the magnetic field produced by the first magnet and second magnet; and
    forming a fistula with the fistula-forming element;
    wherein the first magnet is a focused magnet characterized by a first magnetization pattern comprising a first plurality of magnetic flux vectors, wherein each of the first plurality of magnetic flux vectors intersects a first magnetic origin; and
    wherein the second magnet is characterized by a second magnetization pattern comprising a second plurality of magnetic flux vectors, wherein each of the second plurality of magnetic flux vectors intersects a second magnetic origin.

2. The method of claim 1, wherein the first magnet comprises a first longitudinal axis and the second magnet comprises a second longitudinal axis, and wherein the first magnetic origin comprises a first line oriented parallel to the first longitudinal axis, and the second magnetic origin comprises a second line oriented parallel to the second longitudinal axis.

3. The method of claim 1, wherein the fistula-forming element is an electrode, and wherein forming the fistula with the fistula-forming element comprises ablating tissue with the electrode.

4. The method of claim 1, wherein the first blood vessel is a vein and the second blood vessel is an artery.

* * * * *